United States Patent [19]

Inoue et al.

[11] Patent Number: 4,670,146
[45] Date of Patent: Jun. 2, 1987

[54] COMPOSITE HYDROPHILIC MEMBRANE AND METHOD FOR MANUFACTURE THEREOF

[75] Inventors: Tadashi Inoue, Fujisawa; Tsumoru Kuwabara, Yokosuka; Kiyotaka Yoshie, Yokohama, all of Japan

[73] Assignee: Asahi Kasei Kogyo Kabushiki Kaisha, Osaka, Japan

[21] Appl. No.: 391,444

[22] Filed: Jun. 23, 1982

[30] Foreign Application Priority Data

Jun. 24, 1981 [JP] Japan .................................. 56-96500

[51] Int. Cl.$^4$ ............................................. B01D 13/00
[52] U.S. Cl. ................... 210/490; 210/500.36; 210/640; 521/27
[58] Field of Search ................... 210/500.2, 638, 321.1, 210/500.36, 640, 490; 521/27, 143; 427/244, 245, 246; 204/296; 264/41, 49

[56] References Cited

U.S. PATENT DOCUMENTS

| | | | |
|---|---|---|---|
| 3,679,538 | 7/1972 | Druin et al. | 161/159 |
| 3,925,332 | 12/1975 | Haito et al. | 521/27 X |
| 3,945,927 | 3/1976 | Imai et al. | 521/27 X |
| 4,199,445 | 4/1980 | Chiang et al. | 210/640 |
| 4,409,339 | 10/1983 | Matsuda et al. | 521/143 |

Primary Examiner—Frank Spear
Attorney, Agent, or Firm—Armstrong, Nikaido, Marmelstein & Kubovcik

[57] ABSTRACT

A composite hydrophilic membrane comprising a very thin semipermeable hydrophilic membrane containing a sulfonic group and a polyethylenic microporous membrane containing sulfonic group. This hydrophilic membrane has specially high permeation rate of water and excellent separation ability.

The composite hydrophilic membrane is manufactured by a method which comprises fusing a very thin membrane containing an ethylenic copolymer onto the surface of a polyethylenic microporous membrane or a polyethylenic membrane capable of being converted into a microporous membrane thereby forming a composite film, converting the resin film prior to and/or during and/or after sulfonation into a microporous membrane, and causing the composite film to react with a sulfonating agent. This method permits easy and efficient production of the composite hydrophilic membrane.

25 Claims, 1 Drawing Figure

COMPOSITE HYDROPHILIC MEMBRANE AND METHOD FOR MANUFACTURE THEREOF

BACKGROUND OF THE INVENTION

From early days, attempts have been made to separate organic compounds as contained in mixtures by the membrane process. Virtually none of them, however, have matured into successful commercialization.

Although the procedural superiority which is inherent in the membrane separation process has found due recognition, the process itself has not been adopted for actual commercial applications. This is mainly because the development of membranes appropriate for the separation of organic compounds as from their mixtures has remained retarded.

The method most popularly adopted to date for the separation of organic compounds as contained in mixtures is distillation. This method has been substantially established from the technical point of view. Unfortunately, however, it has a disadvantage that it cannot be used advantageously for the separation of substances having mutually near boiling points, the separation of azeotropes, and the separation of substances unstable owing to thermal hysteresis. The recent sharp rise in the oil price has urged early development of energy-saving methods for the separation of organic compounds. As one of such methods, the membrane separation process is expected to meet the needs of the times.

To anticipate future exhaustion of the world's oil deposits, the development of substitute energy for oil is a matter requiring immediate attention. Among other promising resources, the biomass has a very bright prospect of being actually adopted as a successful substitute because it has an advantage that it utilizes the solar energy, grows through the process of reproduction, and produces no notable effect upon the natural environment.

The ethanol which is obtained by fermenting the material issuing from the biomass is in the form of an aqueous solution containing ethanol in a concentration of about 10%. For this solution to be used effectively as a substitute energy for oil, it must be treated so as to have its ethanol concentration heightened. When the conventional distillation process is adopted for the purpose of heightening the ethanol concentration of the solution, the energy to be consumed for converting the biomass into the energy of its final form amounts to a huge volume such that the energy obtained from the biomass may possibly be deprived of its value as a substitute energy for oil. In the technology for the development of biomass, the development of a concentration process more efficient than the distillation process constitutes one of the tasks to which the greatest significance is attached.

Various methods have heretofore been proposed for the purpose of obtaining from mixtures of organic compounds with water, particularly from a mixture of ethanol with water, concentrated ethanol through selective permeation of water.

For example, U.S. Pat. No. 2,953,502 discloses production of concentrated ethanol from a water-ethanol azeotrope by the pervaporation of the azeotrope by use of an acetyl cellulose membrane. This method is reported to have a separation factor of 8.5. For the separation of a water-ethanol azeotrope having a high ethanol concentration, this separation factor is low. Besides, the feasibility of this method is not sufficient because the membrane has much to be desired with respect to thermal resistance and chemical stability. In the Journal of Membrane Science, 1 (1976), pp. 271–287, there is reported a method for the concentration of a water-ethanol azeotrope by use of a membrane having poly(N-vinylpyrrolidone) grafted to polytetrafluoroethylene. In this case, however, the separation factor is 2.9, a value still lower than that obtained by the aforementioned method. Similarly to the membrane used in the aforementioned method, the membrane used in this method is deficient in separation capacity. Japanese Patent Publication No. 10548/1979 and No. 10549/1979 also teach methods for the separation of mixtures of organic compounds with water. These methods, however, lack feasibility in terms of the permeation rate.

From the disclosures such as of Japanese Patent Publication No. 41035/1976, Japanese Patent Publication No. 29988/1977, and U.S. Pat. No. 3,925,332, it has already been known to the art that hydrophilic membranes having an ion-exchange ability are obtained from ethylenic copolymer films by quick, uniform incorporation of a sulfonic group throughout the entire thickness of such films.

Further from the disclosure of U.S. Pat. No. 3,925,332, it has been known to the art that a hydrophilic membrane having an ion-exchange ability is similarly obtained from a film of a resinous composition comprising an ethylenic copolymer and a thermoplastic resin relatively inactive to the sulfonating agent.

These hydrophilic membranes have been developed as electroporous type membranes intended for uses as ion-exchange membranes, diaphragms in electrolytic cells, and membranes for dialysis. They are specific membranes in respect that, in addition to outstanding ion-exchange ability, they exhibit a high barrier property to anions, offer only a small degree of electric resistance in electrolytes, and retain the flexibility peculiar to ethylenic copolymers.

Although these hydrophilic membranes possess extremely high chemical stability in aqueous solutions of pH values ranging from the strong acidic zone through the neutral zone and the alkali zone, they have a disadvantage that they are gradually deteriorated by the action of oxidative chemicals and their various properties are accordingly degraded. The hydrophilic membranes have another disadvantage that since they assume large water contents in aqueous solutions and consequently exhibit high degrees of area swelling, they have weak strength in aqueous solutions. This particular disadvantage goes to restrict the usefulness of the hydrophilic membranes in proportion as their electric resistance in electrolytes is lowered and their thickness is decreased.

Concerning the use of the hydrophilic membrane obtained by incorporating a sulfonic group in an ethylenic copolymer as a diaphragm in a lead cell, there has been proposed in Japanese Publication of Unexamined Patent Application No. 140543/1978 a diaphragm for separating an anode and a cathode in the electrolytic cell, which diapharagm is obtained by using any of the hydrophilic membranes heretofore known in the art as described above and a varying reinforcing material such as, for example, a woven, knit, or non-woven fabric of inorganic fibers such as glass fibers, asbestos fibers, alumina fibers, or zirconia fibers which are bad conductors of electricity and are resistant to sulfuric acid or a woven, knit, or non-woven fabric or porous membrane of organic high molecular compounds such as polyethylene, polypropylene, rubber, nylon, polyester, or cellulose which is a bad conductor of electricity and is resistant to sulfuric acid.

The primary object of this diaphragm resides in precluding otherwise possible oxidative degradation of the hydrophilic membrane by preventing the hydrophilic membrane from being directly exposed to contact with the electrode. Further, owing to the physical combination of the hydrophilic membrane and the varying reinforcing material, the composite membrane so produced becomes easier to handle as during the assembly of a lead cell and serves advantageously as a diaphragm for the lead cell. In the production of this diaphragm, since the hydrophilic membrane to be used therein is prepared by one of the known methods such as of U.S. Pat. No. 3,925,332, it is extremely difficult for the hydrophilic membrane to be obtained in an extremely small thickness. Namely, when the membrane thickness is decreased to not more than 10 μm, the strength of the membrane is so inferior in the sulfonation bath during or after sulfonation that the membrane is readily torn or broken. Therefore, it is difficult to sulfonate the membrane continuously and stably, and to remove the membrane from the sulfonation bath. This constitutes a serious problem in view of the commercial continuous production process. When the hydrophilic membrane to be used has a particularly small thickness, it exhibits poor resistance to oxidative degradation and the lead cell using this membrane offers a short life cycle. To meet the purpose of this particular invention, therefore, the hydrophilic membrane is desired to have a thickness in the neighborhood of about 40 μm as indicated in the examples cited herein below.

SUMMARY OF THE INVENTION

This invention provides a composite hydrophilic membrane which is produced by incorporating a sulfonic group into a composite film having a very thin film containing an ethylenic copolymer adhered to a polyethylenic microporous membrane or a polyethylenic resin film capable of being converted into a microporous membrane and which, therefore, comprises a very thin semipermeable hydrophilic membrane containing a sulfonic group and a polyethylenic microporous membrane containing a sulfonic group. This composite hydrophilic membrane (1) permeates water with high selectivity from mixtures of organic compounds with water, (2) has a low permeation coefficient for organic compounds in the electrolyte, (3) permits no easy permeation of lipophilic compounds, (4) possesses an outstanding cation-exchange ability and a barrier property to anions, (5) offers only low degrees of electric resistance in various electrolytes, and (6) possesses a barrier property for zincate ions in alkalis.

This invention also provides a method for the manufacture of a composite hydrophilic membrane, which comprises adhering at least a very thin membrane containing an ethylenic copolymer with the surface of at least a polyethylenic microporous membrane or at least a polyethylenic resin film capable of being converted into a microporous membrane thereby producing a composite film and then causing the composite film to be reacted upon by a sulfonating agent, with the polyethylenic resin film, if used, converted to the microporous membrane either prior to and/or during and/or after the sulfonation. By this method, the aforementioned composite hydrophilic membrane is easily and efficiently produced.

DETAILED DESCRIPTION OF THE INVENTION

Figure 1:
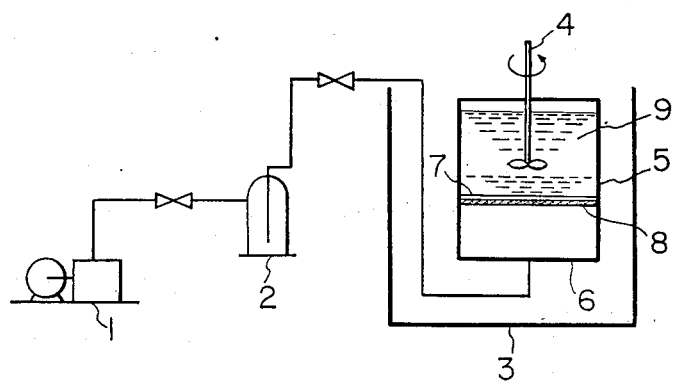
FIG. 1 is an explanatory diagram illustrating a typical apparatus to be used for effecting the membrane of this invention. In the diagram, 1 denotes a vacuum pump, 2 a trap, 3 a constant temperature bath, 4 a stirrer, 5 a feed chamber, 6 a permeation chamber, 7 a membrane, 8 a porous plate, and 9 a feed liquid (a mixture of an organic compound with water).

This invention has been established for remedying the aforementioned problems.

An object of this invention is to provide a membrane which acquires properties appropriate for the purpose of a separating membrane by causing the conventional hydrophilic membrane which is obtained by incorporating a sulfonic group into an ethylenic copolymer to be formed in a uniformly decreased thickness.

Another object of this invention is to provide a hydrophilic membrane which excels in strength and resistance to oxidative degradation despite its small thickness.

Yet another object of this invention is to provide a membrane which exhibits an extremely low electric resistance in electrolytes.

Still another object of this invention is to provide a membrane which, despite its extremely low electric resistance in electrolytes, shows small degrees of area swelling in electrolytes.

A further object of this invention is to provide a composite hydrophilic membrane which, owing to the sulfonation of a reinforcing material incorporated therein, acquires excellent hydrophilicity, water-retaining property, thermal resistance, and solvent resistance.

Now, the present invention will be described in detail below. The composite hydrophilic membrane of the present invention comprises having adhered fast at least two layers formed of a very thin semipermeable hydrophilic membrane derived from an ethylenic copolymer or an ethylenic copolymer resin composition and containing at least one hydrophilic group selected from the class consisting of —OH group and —COOR group (wherein, R is hydrogen, a hydrocarbon group of one to five carbon atoms, an alkali metal atom or other ion capable of forming salt with a carboxyl group) and at least 0.2 meq/g of sulfonic group, and a polyethylenic microporous membrane containing a sulfonic group.

Because the semipermeable hydrophilic membrane has an extremely small thickness and contains a sulfonic group inherently having extremely high hydrophilicity, at least one hydrophilic group selected from the class consisting of —OH group and —COOR group and because the polyethylenic microporous membrane is incorporated as a reinforcing material and this polyethylenic microporous membrane contains a sulfonic group, the composite hydrophilic membrane of the present invention constructed as described above has a particularly high separation factor in the separation of mixtures of organic compounds with water, excels in the permeation rate of water, exhibits excellent thermal resistance, solvent resistance, and mechanical strength, and abounds with hydrophilicity and, therefore, serves ideally as a separation membrane.

To be more specific, the composite hydrophilic membrane of the present invention is a composite membrane which comprises a semipermeable hydrophilic membrane having a thickness in the range of 10 to 0.05 μm, more desirably 5 to 0.05 μm, and most desirably 1 to 0.05 μm and containing at least one functional group selected from the class consisting of —COOR group and an —OH group, the functional group being preferably a hydrophilic group such as a carboxyl group, a carboxylate, or an —OH group, and at least 0.2 meq/g, preferably 1 to 5 meq/g, of a sulfonic group and a sulfonated polyethylenic microporous membrane, preferably a polyethylenic microporous membrane containing at least 0.05 meq/g of a sulfonic group. This composite hydrophilic membrane is obtained by subjecting to sulfonation and optionally to hydrolysis and/or neutralization a composite film which has adhered fast therein at least one very thin film of an ethylenic copolymer having too small film strength and too much flexibility to be continuously reacted upon by a sulfonating agent according to the conventional method and at least a polyethylenic microporous membrane or at least a polyethylenic resin film capable of being converted into at least a microporous membrane prior to or during sulfonation.

The composite hydrophilic membrane has an advantage that the time of the sulfonation reaction can be shortened by amply decreasing the thickness of the thin film containing the ethylenic copolymer and, consequently, otherwise possible undesired side reactions can be minimized. It has another advantage that since it comprises a very thin semipermeable hydrophilic membrane portion having a large separation factor and a high permeation rate and a reinforcement portion excelling in thermal resistance, solvent resistance, mechanical strength, and hydrophilicity, it ideally combines the properties of the two portions for a separation membrane.

In the composite hydrophilic membrane of the present invention, the very thin semipermeable hydrophilic membrane is a homogeneous membrane which retains the properties of a semi-permeable membrane and possesses no micropores. In the gas permeation process or the pervaporation process, this membrane manifests an ability to separate water and alcohol. When the sulfonic group content of this membrane is at least 0.2 meq/g, the composite hydrophilic membrane functions ideally as a separation membrane excelling in separation factor and permeation rate. The composite hydrophilic membrane loses its resistance to oxidative degradation when the sulfonic group content of the semipermeable hydrophilic membrane increases excessively. Thus, the sulfonic group content is desired to be in the range of 1 to 5 meq/g.

The composite hydrophilic membrane of the present invention has the very thin hydrophilic membrane and the microporous membrane adhered fast to each other to form one inseparable body. Even when the thin hydrophilic membrane has a very small thickness and, in the electrolyte, exhibits a very low electric resistance unattainable by the conventional method, it is no longer allowed to swell freely in an aqueous solution. Since the very thin hydrophilic membrane retains its initial swelling property intact even when it is oxidized during use, the composite hydrophilic membrane keeps its properties fast and retains rich durability enough to preclude oxidative degradation. As described above, the composite hydrophilic membrane of the present invention is obtained by the reaction of the sulfonating agent upon the composite film. During this reaction, the microporous surface of the polyethylenic microporous membrane having a large surface area is exposed to the sulfonating agent. Consequently, the composite hydrophilic membrane to be produced by this invention possesses a microporous membrane preponderantly sulfonated in the microporous surface thereof.

Since the polyethylenic microporous membrane contains the sulfonic group preponderantly in the microporous surface thereof, the composite hydrophilic membrane (1) exhibits high affinity for liquids of high surface tension such as water and abounds with wetting property and liquid retaining property, (2) defies fusion by heat and excels in thermal resistance, (3) exhibits very little affinity for organic solvents and, therefore, excels in solvent resistance, and (4) enables the polyethylenic resin as reinforcement to retain high strength and resistance to oxidation because of the absence of the sulfonic group in the greater part of the polyethylenic resin except in the microporous surface thereof.

The composite hydrophilic membrane of this invention, consequently, serves advantageously as a separation membrane for separating or concentrating valuable components from liquid or gaseous mixtures with high selectivity. Particularly it functions ideally as a separation membrane for selectively permeating water from mixtures of organic compounds with water.

As described above, the microporous surface of the composite hydrophilic membrane of the present invention exhibits a high wettable property in liquids of high surface tension such as, for example, water. Thus, it can be advantageously used as a diaphragms in a secondary cell, because the diaphragm which has been partly dried after the level of the electrolyte in the cell has fallen is immediately wetted and is allowed to resume a low electric resistance when the electrolyte is replenished. When the membrane of this invention is used as a diaphragm for diffusion dialysis, the diaphragm once dried because of total consumption of an aqueous solution under treatment can be wetted with the aqueous solution even if it is not wetted in advance with alcohol or glycol. Thus, the diaphragm immediately resumes its function as a dialytic diaphragm.

Further, the microporous surface of the composite hydrophilic membrane of this invention abounds with ability to retain liquids and water as already pointed out. When the membrane is used as a diaphragm for a fuel cell using the fuel as dissolved in the electrolyte wherein the diaphragm is destined to be exposed to contact with an air electrode or oxygen electrode, it has an advantage that the contact resistance on the surface of contact with the electrode is amply low.

As the ethylenic copolymer which is converted into the very thin hydrophilic membrane by being subjected to sulfonation in the present invention, it is preferable to use at least one copolymer selected from the group consisting of an ethylenic copolymer of ethylene with 1 to 18 mol % of a comonomer of the general formula:

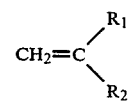

(wherein, R₁ denotes either H or CH₃ and R₂ denotes either OCOR₃ or COOR₄, providing that R₃ is a hydrocarbon group of one to five carbon atoms and R₄ is H, a hydrocarbon group of one to six carbon atoms, an alkali metal atom, or other ion capable of forming a salt with a carboxyl group) and a saponification derivative of the ethylenic copolymer. Namely, the ethylenic copolymer is a copolymer of ethylene with 1 to 18 mol % of a comonomer of the general formula:

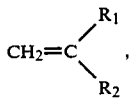

a copolymer of ethylene with the aforementioned comonomer and containing a small amount of a monomer other than ethylene falling within the range not departing from the purpose of this invention, or a saponification derivative of the aforementioned ethylenic copolymer. Since the film containing the ethylenic copolymer has a very small thickness as used in the present invention, even when the content of the comonomer component in this copolymer is smaller than in the hydrophilic membrane to be obtained by incorporating a sulfonic group in the film of the conventional ethylenic copolymer, the produced hydrophilic membrane acquires the properties aimed at by the present invention. The preferable composite hydrophilic membrane is obtained when the content of the aforementioned comonomer component in the ethylenic copolymer falls in the range of 1 to 18 mol %. The expression "ethylenic copolymer" as used in the present invention denotes an ethylenic copolymer capable of being converted prior to, after, or during sulfonation into a very thin hydrophilic membrane containing at least one hydrophilic group selected from the class consisting of —OH group and —COOR group and at least 0.2 meq/g of sulfonic group almost uniformly in sectional direction of a very thin film. For example, it is at least one ethylenic copolymer selected from the group consisting of an ethylenic copolymer of ethylene with a comonomer of the general formula:

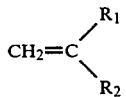

[wherein, R₁ denotes either H or CH₃ and R₂ denotes either OCOR₃ or COOR₄ (providing that R₃ is a hydrocarbon group of one to five carbon atoms and R₄ is H, a hydrocarbon group of one to six carbon atoms, an alkali metal atom, or other ion capable of forming salt with carboxyl group)] and a saponification derivative of the ethylenic copolymer. And, the expression "ethylenic copolymer resin composition" as used in the present invention means a resinous composition containing at least 15% by weight of said ethylenic copolymer and at most 85% by weight of other thermoplastic resin. It is needless to say that in the present invention there may be used the ethylenic copolymer obtained from other comonomer besides the aforementioned comonomer within the scope not departing from the object of the present invention.

At least one ethylenic copolymer selected from the group consisting of ethylene-vinyl acetate copolymer, saponified ethylene-vinyl acetate copolymer, ethylene-methyl methacrylate copolymer, ethylene-methacrylic acid copolymer, metallic salts of ethylene-methacrylic acid copolymer, metallic salts of ethylene-methyl methacrylate-methacrylic acid copolymer, ethylene-ethyl acrylate copolymer, ethylene-acrylic acid copolymer, and metallic salts of ethylene-acrylic acid copolymer proves to be advantageously usable because the copolymer itself enjoys good moldability and high reactivity with the sulfonating agent and the sulfonated membrane enjoys high water resistance.

The expression "other thermoplastic resin" as used in this invention means a thermoplastic resin which can be blended rather uniformly with the aforementioned ethylenic copolymer or the saponification derivative of the ethylenic copolymer and is relatively inactive with the sulfonating agent. At least one thermoplastic resin selected from the group consisting of polyethylene, polypropylene, 1,2-polybutadiene, and polybutene-1 can be advantageously used. The hydrophilic membrane obtained from the very thin film containing this thermoplastic resin is eventually converted into a composite hydrophilic membrane abounding in resistance to oxidative degradation.

The amount of the thermoplastic resin to be incorporated in the resin composition is 85% by weight at most. When the content of the thermoplastic resin exceeds this upper limit, the reaction time of the composite film with the sulfonating agent is excessively lengthened and the produced composite hydrophilic membrane fails to permeate water at a desirable rate and, therefore, fails to fulfil its function. In the present invention, since the film of ethylenic copolymer is very thin, it has an advantage that the aimed hydrophilic membrane can be obtained even if the content of the comonomer component is small in comparison with the conventional hydrophilic membrane which is obtained by incorporating sulfonic group into ethylenic copolymer film. Even if the content of the comonomer component is large, it is possible to prevent a trouble due to blocking property of the film prior to sulfonation by a method of adding other thermoplastic resin or by making the layer construction such as microporous membrane/very thin film/microporous membrane. Therefore, it has an advantage that the comonomer component can be suitably selected within the scope not departing from the object of the present invention, and it is specially preferable to use the ethylenic copolymer obtained from 1–18 mol % of a copolymer of the general formula:

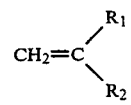

in view of the reaction time of sulfonation, separation ability, mechanical strength, and resistance to oxidation degradation. When it is smaller than the lower limit 1 mol %, the time of sulfonation is elongated and side reactions besides the sulfonation occur readily, so that the obtained very thin hydrophilic membrane becomes brittle and so, it is required to handle with care. Besides, uses are limited because of inferior separation ability due to the small amount of hydrophilic group selected from the class consisting of —OH and —COOR group.

Conversely, when it exceeds the upper limit 18 mol %, to prevent occurence of blocking of the very thin film, it becomes necessary to add a large amount of other thermoplastic resin or form the aforementioned layer construction for obtaining a practical membrane.

Consequently, the obtained composite hydrophilic membrane acquires a low permeation rate of water or its production method is restricted. As the result, the aforementioned range of 1-18 mol % is most suitable.

The expression "other ion capable of forming a salt with a carboxyl group" as used in the present invention means at least one member selected from the group consisting of divalent metallic ions such as $Mg^{2+}$, $Ca^{2+}$, $Zn^{2+}$, and $Ba^{2+}$, trivalent metallic ions such as $Al^{3+}$, and cations such as $NH_4^+$ which form salts with $-COO-$ group. It is self-evident that the sulfonic group used in the present invention can be used, similarly to the carboxyl group, in a state forming a salt with an alkali metal or some other cation besides $-H$. Thus, specific examples of other cation include divalent metallic ions such as $Mg^{2+}$, $Ca^{2+}$, $Zn^{2+}$, and $Ba^{2+}$, trivalent metallic ions such as $Al^{3+}$, and $NH_4^+$ which are capable of forming salts with a sulfonic group.

The expression "polyethylenic microporous membrane or polyethylenic resin film capable of being converted into a microporous membrane" as used in this invention means a polyethylenic microporous membrane or a polyethylenic resin film which can be adhered fast to the aforementioned very thin film containing an ethylenic polymer and retained fast thereto without being peeled off during sulfonation or during end use, the former polyethylenic microporous membrane at temperatures in a range in which most of the micropores thereof remain uncrushed by the melting and the latter polyethylenic resin film at temperatures not specifically restricted. It is self-evident that the polyethylenic microporous membrane or the polyethylenic resin film to be selected should possess a reinforcing effect and, on being sulfonated, acquire the permeation rate of water, electric resistance and area swelling ratio in the electrolyte which invariably are amply lower than the corresponding physical constants of the composite hydrophilic membrane desired to be produced. The method to be adopted for the manufacture of the polyethylenic microporous membrane or polyethylenic resin film is not specifically restricted. The method disclosed in Japanese Publication of Unexamined Patent Application No. 74057/1976, for example, effects this manufacture by mixing polyethylene with a powdered inorganic substance having a liquid organic substance such as dioctyl phthalate adsorbed thereon in advance, melting the resultant mixture and molding the molten mixture in the shape of a film, and subsequently extracting from the resultant film the liquid organic substance either alone or in combination with the powdered inorganic substance. By this method, the polyethylenic microporous membrane is obtained after the step of extraction and the polyethylenic resin film before the extraction. This particular method proves to be advantageous in respect that the porosity of the microporous membrane is freely controllable, the average pore diameter is relatively small, and the membrane or film is capable of being stretched.

Otherwise, by a procedure which comprises mixing polyethylene with a varying substance destined to be extracted afterward, melting the resultant mixture and molding the molten mixture in the shape of a film, and subsequently extracting from the produced film the aforementioned substance, a polyethylenic microporous membrane is obtained at the end of the step of extraction or a polyethylenic resin film before the step of extraction. Those polyethylenic microporous membranes or polyethylenic resin films capable of being converted into microporous membranes by stretching or before or during or after sulfonation which are manufactured by various other methods also answer the description.

The aforementioned polyethylenic microporous membrane or polyethylenic resin film may contain various resins therein within a range not departing from the object of this invention. Rather in applications for which sulfonation of the microporous membrane is highly desirable, the polyethylene may contain therein up to 50% by weight of at least one of the aforementioned ethylenic copolymers.

The porosity, average pore diameter, and pore diameter distribution of the microporous membrane are not particularly limited but may be properly selected, depending on the method of manufacture adopted and the use contemplated for the composite hydrophilic membrane. Generally, before complexing the very thin film the microporous membrane is desired to have porosity in the range of 20 to 80% and average pore diameter of the surface openings in the range of 0.005 to 10 $\mu$m, preferably 0.01 to 1 $\mu$m, and a narrow (uniform) pore diameter distribution, because it excels in preclusion of occurrence of pinholes, permeation rate of water, repression of electric resistance, adhesive strength, uniformity of adhesion, and mechanical strength particularly when the micropores contained therein satisfy the conditions mentioned above. When the aforementioned composite film is prepared by incorporating the microporous membrane described above, it may be sulfonated, either in an unstretched state or in a stretched state, by reaction with a sulfonating agent so as to incorporate a sulfonic group in the microporous surface thereof.

Similarly when the composite membrane is prepared by incorporating a polyethylenic resin film which is designed to be converted into a microporous membrane, this polyethylenic resin film is desired to be such that the resin film, on being converted into the microporous membrane, assumes porosity, average pore diameter, and pore diameter distribution satisfying the aforementioned conditions before the composite film is stretched. Prior to and/or after stretching and/or during and/or after sulfonation, the resin film portion of the above composite film is converted into the microporous membrane, thereby there is obtained a composite hydrophilic membrane aimed at by the present invention.

The thickness of the microporous membrane portion of the composite hydrophilic membrane may be properly selected, depending on the method of manufacture, the intended use, and the thickness of the composite hydrophilic membrane to be obtained. From the standpoint of the effect in reinforcement and the convenience of handling, this thickness generally is preferred to fall in the range of about 10 $\mu$m to 1 mm.

The ratio of the thickness of the microporous membrane to that of the very thin hydrophilic membrane may be properly fixed in close relation to such factors as electric resistance in the electrolyte, number of layers of microporous membrane and very thin hydrophilic membrane, and thickness of the composite hydrophilic membrane. Generally, this is preferred to be increased in proportion as the thickness of the very thin hydrophilic membrane decreases and/or the sulfonic group content in the electrolyte increases. Generally, the composite hydrophilic membrane contemplated by the present invention is obtained when this ratio falls in the range of about 0.5 to 1000.

The composite hydrophilic membrane of the present invention is derived from a composite film wherein at least one very thin film of an ethylenic copolymer of the aforementioned specific chemical structure and a polyethylenic microporous membrane or a polyethylene resin film capable of being converted into a microporous membrane adhered fast to each other. The expression "adhered fast" as used in this invention is used to describe a condition in which the substance making up one of the aforementioned two membranes (or one membrane and one resin film) is melted or softened along the interface between the two layers and is solidified after wetting the surface of the substance of the other membrane, or the substances of the two membranes are fused to each other, or the substance of one of the two membranes is softened or melted, forced into the recesses on the surface of the other membrane and solidified as anchored therein, or the two adjoining layers are intimately and powerfully united by varying combinations of the situations described above. Practically, this expression signifies such union of the two layers that they are not separated along the interface thereof when they are normally treated in manufacturing or subjected to a chemical treatment for sulfonation, or a treatment for formation of micropores. This fast union of the two membranes can be accomplished by an operation utilizing the action of heat, pressure, or the combination of such actions.

In the present invention, the adhesion of the very thin film of the ethylenic copolymer with the polyethylenic microporous membrane or the polyethylene resin film capable of being converted into a microporous membrane is desired to be carried out uniformly and fast throughout the entire surface of the film or membrane to be adhered. If there are portions which are not adhered or which are not provided with enough adhesive strength, it is not desirable because during sulfonation the very thin film portion is heavily swelled thereby causing bubbles and lack of uniformity in the treatment when a large amount of sulfonic group is incorporated in the very thin film of the ethylenic copolymer possessing the aforementioned specific structure.

For the composite hydrophilic membrane of the present invention, the combination of its component layers, i.e. microporous membrane(s) and very thin hydrophilic membrane(s), is not specifically limited. From the standpoints of performance and economy, the combinations of very thin hydrophilic membrane/microporous membrane, microporous membrane/very thin hydrophilic membrane/microporous membrane, and very thin hydrophilic membrane/microporous membrane/very thin hydrophilic membrane prove to be preferable. Particularly for uses in which the composite hydrophilic membrane serves to separate mixtures, the combination of microporous membrane/very thin hydrophilic membrane/microporous membrane proves to be advantageous in terms of efficiency of separation, resistance to wear, resistance to scratches, and resistance to contamination.

Generally, a microporous membrane containing polyethylene alone or in combination with an ethylenic copolymer is destitute of hydrophilicity and, therefore, exhibits poor wetting property to aqueous solutions such as electrolytes. Although the composite hydrophilic membrane of this invention has only a small sulfonic group content for its exchange capacity, it is sulfonated preponderantly in the microporous surface region and, therefore, is improved in hydrophilicity as well as in resistance to heat and solvents. Where the composite hydrophilic membrane is desired to offer still higher hydrophilicity by reason of the nature of intended use or it is required to possess still higher stability enough to withstand handling in the atmosphere, it may be given enhanced affinity for water, improved water-retaining property, or heightened physical stability by any of the known methods such as, for example, the method which resorts to the treatment of impregnation with a hydrophilic compound selected from among glycerin, polyethylene glycol, and various alcohols. Naturally this additional treatment proves to be advantageous for the betterment of the performance of the composite hydrophilic membrane.

The content of the sulfonic group in the aforementioned microporous membrane is to be determined by the porosity, pore diameter, and thickness of the microporous membrane, the kind of the material making up the membrane (high-density polyethylene, medium-density polyethylene, low-density polyethylene, or ethylenic copolymer, and other organic or inorganic compounds added), and the object and effect of the membrane. Generally, the composite hydrophilic membrane enjoys significant improvement in hydrophilicity, resistance to heat, and resistance to solvents when the microporous membrane is formed of a high-density polyethylene having porosity in the range of 50 to 90%, average pore diameter in the range of 0.01 to 1 $\mu$m, and sulfonic group content of at least 0.05 meq/g of the microporous membrane in terms of exchange capacity. If the composite hydrophilic membrane of this invention is excessively sulfonated, though never beyond the level of 1 meq/g under ordinary conditions, there is a possibility that the reinforcing effect of the porous membrane will fall short of the expected level in terms of strength, swelling property in aqueous solutions, and resistance to oxidative degradation. It is, therefore, desirable to select the material of the microporous membrane by taking into due consideration the kind and thickness of the very thin film and the electric resistance of the composite hydrophilic membrane and avoid sulfonating the composite hydrophilic membrane excessively.

As described above, the composite hydrophilic membrane of this invention excels particularly in properties necessary for a separation membrane. Thus, it is used advantageously as a separation membrane in various methods of separation directed to diffusion dialysis, reverse osmosis, pervaporation, and gas permeation, etc.

Now, the composite hydrophilic membrane of this invention will be described below with reference to its utility as a separation membrane by the method of pervaporation and the method of gas permeation.

The expression "utility of the composite hydrophilic membrane of this invention by the method of pervaporation and the method of gas permeation" as used in this invention describes an operation in which the feed zone of the composite hydrophilic membrane is kept in contact with a liquid or gaseous mixture and the permeate zone thereof is kept in contact with a carrier gas or kept under a vacuum so that the component compounds of the mixture will be separated and/or concentrated by making use of the difference between the degrees of permeability of the membrane to the component compounds. Among other mixtures, those of organic compounds with water are separated and concentrated particularly advantageously by this method. From these mixtures, liquid or gaseous, the membrane permits permeation of water with high selectivity.

The carrier gas to be used in this operation is not specifically limited. In the case of a mixture of an organic compound with water, for example, air of low humidity proves to be an advantageous carrier gas because a large difference of concentration can be established between the feed zone and the permeate zone of the membrane, separation of air from the compound passed through the membrane can be effected with ease (providing that when the compound thus passed through the membrane contains substantially no organic substance and does not particularly require water, it may be released directly into the ambient air), and the cost of supply of carrier gas is low.

The expression "a mixture of an organic compound with water" as used in this invention means a liquid or gaseous mixture resulting from the combination of at least one organic compound and water. Here, the operation in which the mixture to be brought into contact with the membrane is in a liquid state is called pervaporation and the operation in which the mixture is in a gaseous state is called gas permeation.

As described above, the composite hydrophilic membrane of the present invention is particularly advantageous for selective permeation of water from mixtures of organic compounds with water by the aforementioned method of pervaporation or the method of gas permeation. In this particular operation, the composite hydrophilic membrane functions most desirably when the very thin hydrophilic membrane incorporated therein contains, as the substituent —COOR, at least one hydrophilic group selected from the class consisting of carboxyl group, a carboxylate, or an OH group. The separation factor and the permeation rate of water are enhanced in proportion as the sulfonic group content of the very thin hydrophilic membrane increases. The composite hydrophilic membrane incorporating such a thin hydrophilic membrane permeates water from the mixture of an organic compound with water at high selectivity and at a high rate, to provide effective separation of water and the organic compound.

In accordance with the aforementioned method of pervaporation, the composite hydrophilic membrane of this invention, especially when the very thin hydrophilic membrane portion thereof has a thickness of not more than 1 $\mu$m, functions advantageously as a separation membrane capable of easily separating a mixture of 50 vol % of ethanol with water, at a temperature of 40° C., into water and ethanol at a rate of not less than 1000 g/hr.m$^2$, with the separation factor, $\alpha A/B$ (A=water and B=ethanol), above 2, desirably above 000 g/hr.m$^2$, with the separation factor, $\alpha A/B$ (A=water and B=ethanol), above 2, desirably above 5, more desirably above 10, and most desirably above 20, and the permeation rate of water above 200 g/hr.m$^2$, preferably above 500 g/hr.m$^2$. Since the composite hydrophilic membrane of this invention excels in resistance to heat, the permeation rate of water in the aforementioned separation can be increased further by elevating the temperature of the mixture under treatment.

Despite the very high affinity which water and ethanol have for each other, the composite hydrophilic membrane of the present invention provides highly selective permeation of water from the mixture of ethanol with water. This high selectivity in the water permeation may be logically explained by a postulate that the active sulfonic group and the other functional group, preferably hydrophilic functional group cooperatively dissolve the interaction between water and ethanol and, at the same time, cause water to be soluble and diffuse in the very thin hydrophilic membrane, while they hardly cause ethanol to be soluble into the very thin hydrophilic membrane and instead suffer it to remain intact on the feed zone of the composite hydrophilic membrane.

By the method described above, organic compounds of high purity can be easily obtained from various azeotropes of water and organic compounds such as those of water and propanol, water and isopropanol, water and sec. butanol, water and tert. butanol, water and diacetone alcohol, water and tetrahydrofuran, water and dioxane, water and pyridine, and water and hexylamine as well as water and ethanol which have defined separation by the conventional method of distillation.

When the composite hydrophilic membrane of this invention is used as a separation membrane by the aforementioned method of gas permeation, it permits substantially no passage of the organic compound component and provides highly selective permeation of water when the permeate zone of the membrane is kept in an absolutely dry state. While this method of separation is characterized by having a still higher separation factor than the pervaporation method, it has a disadvantage that the permeation rate of water is rather low. Thus, this method is used most advantageously for purposes attainable by permeation of relatively small amounts of water such as in separating water from azeotropes containing water, in separating water from aromatic products without sacrificing their aromatic principles, and in separating water from products emitting offensive odors without liberating the odors, or for purposes necessitating extremely high separation factors.

The mixtures for which the composite hydrophilic membrane of the present invention can be effectively used are not particularly defined except that they are liquid or gaseous mixtures each composed of at least one organic compound and water. Examples of organic compounds forming such mixtures include monohydric alcohols represented by methanol, ethanol, propanol, butanol, pentanol, hexanol, octanol, and cyclohexanol; dihydric alcohols represented by ethylene glycol; trihydric alcohols represented by glycerin; ketones represented by acetone, methyl ethyl ketone, and cyclohexanone; ethers represented by dimethyl ether, diethyl ether, tetrahydrofuran, dioxane, methyl cellosolve, and ethyl cellosolve; organic acids represented by formic acid, acetic acid, propionic acid, acrylic acid, methacrylic acid, crotonic acid, maleic acid, half ester of maleic acid, and maleic anhydride; amines represented by methylamine, ethylamine, and ethylene diamine; esters represented by methyl acetate, ethyl acetate, vinyl acetate, acrylic esters, methacrylic esters, crotonic esters, and maleic diesters; hydrocarbons represented by butane, pentane, hexane, octane, cyclohexane, cyclohexene, benzene, toluene, xylene, styrene, and ethyl benzene; nitrogen-containing solvents represented by acetamide, N-methyl acetamide, N,N-dimethyl acetamide, nitrobenzene, dimethyl formamide, and nitroethane; sulfur-containing solvents represented by dimethyl sulfoxide and carbon disulfide; halogen-containing solvents represented by chloroform, carbon tetrachloride, monochlorobenzene, monochloro-acetic acid, and 1,1,1-trichloroethane, and other organic compounds which are gaseous, liquid, or solid at normal room temperature.

Among the mixtures of organic compounds with water described above, those which form homogeneous mixed solutions at normal room temperature can be easily treated by the composite hydrophilic membrane of this invention in accordance with the method of gas permeation or the method of pervaporation. The method of membrane separation is not very effective by any practical standard in separating the mixtures of organic compounds with water which form heterogeneous mixed solutions at normal room temperature. In the concentration of coffee decoction, fruit juices, and other similar tasty beverages which require separation of water without loss of flavors and in the removal of substances of offensive odors or noxious substances, the aforementioned method can be advantageously used to effect required separation of water.

Because the composite hydrophilic membrane of this invention exhibits excellent resistance to solvents, it naturally follows that it can efficiently and consistently separate water even from various mixtures of organic compounds containing less than 1% by weight of water. The composite hydrophilic membrane is particularly suitable for the separation of minute amounts of water from organic solvents containing stabilizer and other additives without entailing loss of such additives.

For the composite hydrophilic membrane of this invention to be used advantageously for effecting highly selective permeation of water from a given mixture by the method of pervaporation or the method of gas permeation, since the membrane is capable of permeating water at a high rate, it is desirable that the flow volume of the carrier gas should be increased or an ample vacuum should be maintained on the permeate zone of the membrane so as to keep the steam concentration at as low a level as possible and the mixture should be kept under thorough stirring so as to preclude possible concentration polarization on the feed zone of the membrane to the fullest possible extent.

Observance of these rules is especially required for those mixtures of organic compounds with water which contain water in large proportions, because the separation factor and the permeation rate of water are both lowered when the concentration of steam on the permeate zone of the membrane approximates the vapor pressure of water.

The affinity of the water or the organic compound of the mixture and the dissociability of the mixture in water vary and, as a natural consequence, the separability of the mixture vary, depending on the kind of the counter ion of carboxyl group and/or sulfonic group in the composite hydrophilic membrane of the present invention. It is, therefore, desirable for the kind of the counter ion to be properly selected to suit the method of separation, the kind of mixture, and the purpose of separation. When the ethanol-water mixture of a low ethanol concentration obtained by the fermentation of the material from biomass is concentrated by the composite hydrophilic membrane of this invention in accordance with the method of pervaporation, for example, the separation factor may be maintained at a high level by selecting such a counter ion as $Ba^{2+}$ which has a relatively low degree of dissociability. Conversely, in the case of an azeotrope of ethanol and water wherein the permeation rate of water is low, it is desirable to maintain the permeation rate of water at a high level by selecting such a counter ion as $K^+$ or $Na^+$ which is rich in coordinated water.

By use of the composite hydrophilic membrane of this invention, it has now become feasible to produce ethanol of high purity from the ethanol-water mixture of a low ethanol content obtained by the fermentation of the material from biomass at a very low energy consumption owing to effective utilization of the heat of atmosphere, the heat of hot plant effluent, the heat of reaction generated during fermentation, or other similar waste heat which has to date had no appreciable economic value.

Other uses are found for the composite hydrophilic membrane of the present invention. For example, it can be used for the separation of mixtures which contain such gaseous inorganic components as He-air and He-$CH_4$.

Further, owing to the catalytic activity of the sulfonic group, —$SO_3H$, the composite hydrophilic membrane of the present invention is capable of synthesizing an ester from an alcohol and an organic acid, for example. In accordance with the aforementioned method of pervaporation, the mixture of alcohol and organic acid is placed in contact with the feed zone of the membrane. Consequently, the membrane quickly permeates water and releases it on the permeate zone, optionally allowing the reaction to proceed in the desired direction of equilibrium. Thus, the composite hydrophilic membrane of this invention is characterized by being utilized for various reaction systems by virtue of the catalytic activity and/or permselectivity of the sulfonic group, —$SO_3H$.

The composite hydrophilic membrane of the present invention is further characterized by having low values of electric resistance in electrolytes. The very thin semipermeable hydrophilic membrane adhered fast to the microporous membrane imparts strength to the whole composite hydrophilic membrane and helps the whole membrane to retain its shape steady. Thus, the composite hydrophilic membrane serves advantageously as a separation membrane having an electric resistance of the order of 0.01 $\Omega.cm^2$ in alkalis, a value which has never been attained by the conventional membrane.

Besides the aforementioned properties manifested during membrane separation, the composite hydrophilic membrane of this invention exhibits properties peculiar to an ethylenic copolymer film containing a sulfonic group, such as (1) high ability to exchange cations and bar passage of anions, (2) low electric resistance in various electrolytes (5 to 0.01 $\Omega.cm^2$ in alkalis, for example), (3) ability to obstruct passage of zincate ion in alkalis, (4) low permeation coefficient of various organic compounds in the various electrolyte, and (5) ability to retard passage of lipophilic compounds. The composite hydrophilic membrane, therefore, may be used not merely for membrane separation as described above but also for various other purposes, for example, (1) as cation-exchange membrane (membrane for electrodialysis, for electrolysis, and for electric osmosis), (2) as separator in various cells represented by Ni-Zn alkali secondary cell, (3) as diaphragm in fuel cells using the fuel as dissolved in the electrolyte, and (4) as smoke casing. These applications make use of the composite hydrophilic membrane's properties including low electric resistance, ability to bar passage of anions, permselectivity, and ability to retard passage of lipophilic compounds.

To be more specific, the composite hydrophilic membrane of this invention may be used as a diaphragm for electrodialysis when the cation transference number thereof is 0.90 or over; as a separator for a nickel-zinc alkali cell when the degree of zinc ion permeability is 2000 μg/hr.cm² at most and the electric resistance in alkali is not more than 2 Ω.cm², preferably not more than 1 Ω.cm²; as a separator for various cells using dilute sulfuric acid as the electrolyte when the electric resistance of the membrane in the dilute sulfuric acid is not more than 5 Ω.cm², preferably not more than 1 Ω.cm²; as a diaphragm for the system of dehydration from aqueous gel and past by electric osmosis; and as a smoke casing when the permeation rate of water is high and the membrane strength is high. And, the composite hydrophilic membrane of this invention is used or manufactured in various shapes such as flat, bag, spiral and hollow depending on the use aimed at. Generally, the hollow fiber having its outside diameter in the range of 5 mm to 50 μm is readily used from the viewpoint of strength.

The fact that the composite hydrophilic membrane of this invention has low electric resistance in various electrolytes, exhibits high ability to exchange cations and bar passage of zincate ion in alkalis, and excels in ability to separate mixtures of organic compounds with water as described above strongly implies that the very thin semipermeable hydrophilic membrane in the composite hydrophilic membrane of this invention has a construction, which (1) contains no pinhole, (2) has an extremely small, uniform thickness, and (3) has sulfonic group homogeneously distributed therein.

Now, the method by which the composite hydrophilic membrane of the present invention is to be manufactured will be described below. In one aspect, this method comprises preparing an aqueous dispersion containing an ethylenic copolymer derived from at least two monomers ethylene and a comonomer of the general formula:

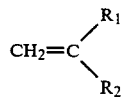

[wherein, $R_1$ denotes H or $CH_3$ and $R_2$ denotes either $OCOR_3$ or $COOR_4$ (providing that $R_3$ is a hydrocarbon group of one to five carbon atoms and $R_4$ is H, a hydrocarbon group of one to six carbon atoms, an alkali metal atom, or other ion capable of forming a salt with carboxyl group)], applying this aqueous dispersion to a polyethylenic microporous membrane or a polyethylenic resin film capable of being converted prior to and/or during sulfonation into a polyethylenic microporous membrane, allowing the applied layer of said ethylenic copolymer to adhere fast to the microporous membrane or the resin film thereby poducing a composite film, converting the resin film prior to and/or during and/or after sulfonation into a microporous membrane, and causing the composite film to be reacted upon by a sulfonating agent.

In the present invention, as the method for applying the aqueous dispersion to the microporous membrane or the resin film, a coating method utilizing a coating rod, air-knife and other instruments is particularly effective for forming a very uniformly applied layer of the dispersion. Besides, there may be adopted a method of spraying the aqueous dispersion with an air gun or a method of immersing the microporous membrane or the resin film in the aqueous dispersion. And, by a method of forming the applied layer (very thin film) of the aqueous dispersion and adhering fast the applied layer to the microporous membrane or the composite film, a composite film can be produced by the ordinary method, for example, evaporating the water content at room temperature or by heating, and conducting heat treatment or hot pressing.

Addition or application of ethanol, propyl alcohol, ethylene glycol, glycerine, or other compound capable of improving wettability to the aqueous dispersion and/or the microporous membrane or the resin film prior to the application of the aqueous dispersion to the microporous membrane or the resin film proves to be advantageous from the standpoint of uniformization of membrane thickness, preclusion of occurrence of pinholes, and enhancement of strength of adhesion.

Further for the hydrophilic membrane to be formed in a very small thickness, it is particularly effective to dilute the aqueous dispersion such as with water so as to apply the aqueous dispersion in a low concentration and/or stretch the membrane itself in at least one direction prior to sulfonation. By this method, there may be manufactured a composite hydrophilic membrane in which the very thin, semipermeable hydrophilic membrane has a thickness of about 0.05 μm.

When two very thin hydrophilic membranes of an equal thickness of not more than 1 μm are produced, one by the method involving dilution of the aqueous dispersion such as with water and the other by the method involving stretching of the membrane prior to sulfonation, and they are compared, it is found that the product of the latter method excels that of the former method in ability to separate mixtures. This method of stretching, therefore, is particularly effective in producing advantageously the very thin hydrophilic membrane.

In the composite film, the porosity and the average pore diameter possessed by the polyethylenic microporous membrane before the composite film is stretched are increased significantly after the composite film is stretched. This stretching, therefore, has an advantageous effect of enhancing the reactivity of the polyethylenic microporous membrane with the sulfonating agent, enabling the sulfonation of the membrane to be completed in a very short time, heightening the permeation rate of water, and lowering the electronic resistance of the membrane in electrolytes.

When the microporous membrane or the resin film is properly selected, it can be stretched generally at temperatures in the range of 50° to 130° C. in an area stretching ratio of not less than 2, preferably not less than 4. Then, by subjecting the composite film immediately to sulfonation or by effecting the sulfonation after conversion of the resin film into a microporous membrane as called for by occation, there is obtained the composite hydrophilic membrane aimed at by this invention.

Even if the thickness of the very thin hydrophilic membrane is extremely small, the microporous membrane offers a reinforcing effect which enables the produced composite hydrophilic membrane to manifest mechanical strength and resistance to oxidative degradation enough to suit intended uses.

The expression "aqueous dispersion of an ethylenic copolymer" as used with respect to the method of this invention for the manufacture of the composite hydrophilic membrane describes a condition in which the aforementioned ethylenic copolymer is dispersed, either independently or in a state incorporating therein a surface active agent, in water. The sole requirement to be met by this aqueous dispersion is that the particles dispersed in water should possess an average particle diameter of about 0.01 to 0.5 μm. Satisfaction of this requirement is important for the manufacture of the composite hydrophilic membrane as aimed at.

As the ethylenic copolymer used in the present invention, preferable results can be obtained by using a copolymer of ethylene with 1 to 18 mol % of a comonomer of the general formula:

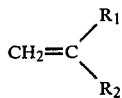

or a copolymer of ethylene with 1 to 18 mol % of a comonomer of the general formula:

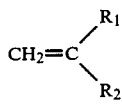

and a small amount of other comonomer, providing that this copolymer is capable of forming an aqueous dispersion upon incorporation into water. Preferably, this ethylenic copolymer is at least one member selected from the group consisting of ethylene-vinyl acetate copolymer, ethylenemethyl methacrylate copolymer, ethylene-methacrylic acid copolymer, metal salts of ethylene-methacrylic acid copolymer, metal salts of ethylene-methyl methacrylate-methacrylic acid copolymer, ethylene-ethyl acrylate copolymer, ethylene-acrylic acid copolymer, and metal salts of ethylene acrylic acid copolymer.

In accordance with the method of manufacture described above and in consideration of economy and practical utility, it is desirable for the composite hydrophilic membrane to be manufactured in a layer combination of very thin hydrophilic membrane/microporous membrane, very thin hydrophilic membrane/ microporous membrane/very thin hydrophilic membrane, or microporous membrane/very thin hydrophilic membrane/microporous membrane.

The conventional method has entailed a problem that when a highly stretched and oriented ethylenic copolymer film is caused to react with a sulfonating agent, it is shrunken significantly during the sulfonation. In accordance with the present invention, since the composite hydrophilic membrane has adhered fast therein a reinforcing material of either a microporous membrane or a resin film capable of resisting the shrinkage of the ethylenic copolymer during the sulfonation, the stretched composite film is retained steadily in the course of the sulfonation by the reinforcing material, with the result that the sulfonation will be completed without causing much shrinkage of the composite film.

Now, the reaction of the composite film with the sulfonating agent which is carried out for the completion of the composite hydrophilic membrane of the present invention will be described in detail below. This reaction is accomplished by using, as the sulfonating agent, fuming sulfuric acid alone, sulfur trioxide or chlorosulfonic acid alone or optionally diluted with a solvent, or sulfur trioxide prepared in the form of a complex compound. Preferably, the reaction is advantageously effected by using fuming sulfuric acid containing 5 to 30% by weight of sulfur trioxide. Although the temperature and time of the sulfonation are not particularly limited, the sulfonation proceeds advantageously at temperatures of not more than 60° C. for a period of two hours at most, preferably for not more than one hour. These temperature and time conditions are preferred because, under such conditions, the sulfonation proceeds without appreciably involving other side reactions. By properly selecting the conditions within the ranges mentioned above, therefore, the composite hydrophilic membrane aimed at by this invention can be obtained with high consistency. After the reaction with the sulfonating agent, the reaction solution adhering to the membrane is diluted and thoroughly washed with water. Then the produced membrane is neutralized with an alkaline reagent such as potassium carbonate or potassium hydroxide, washed thoroughly again with water, and dried as occasion demands before it is put to use. While the ethylenic copolymer containing an ester group is washed and/or neutralized with alkali, a considerable quantity of the ester group is hydrolyzed. Optionally, the composite hydrophilic membrane aimed at by the present invention may be effectively obtained by hydrolyzing the ester with an acid or an alkali as occasion demands. It goes without saying that in the method of this invention for the manufacture of the composite hydrophilic membrane, the method which imparts to the composite hydrophilic membrane desired electric resistance in electrolytes by causing the sulfonated membrane to be briefly treated with a suitable bleaching agent or oxidizing agent may be incorporated.

By the method described above, the composite hydrophilic membrane of the present invention can be manufactured with high efficiency and consistency.

The method of the present invention for the manufacture of the composite hydrophilic membrane enables the properties peculiar to the sulfonated membrane of ethylenic copolymer to be retained intact, permits the thickness of the very thin hydrophilic membrane to be significantly decreased, and the polyethylenic microporous membrane to be appropriately sulfonated. The composite hydrophilic membrane manufactured by this method, therefore, serves ideally as a separation membrane excelling in hydrophilicity as well as in resistance to heat and solvents.

Preferably, the composite hydrophilic membrane may be produced in the shape of a hollow fiber, because it has a large membrane surface area per unit volume.

The method for manufacturing the composite hydrophilic membrane in the shape of a hollow fiber will be described below. This method comprises applying the aforementioned aqueous dispersion of ethylenic copolymer to the inner and/or outer wall surface of a hollow fiber of polyethylenic microporous membrane or a polyethylenic resin film capable of being converted into a microporous membrane, allowing the applied layer of ethylenic copolymer to adhere fast to the hollow fiber of the microporous membrane or resin film, and thereafter allowing the resultant composite film in the shape of a hollow fiber to be reacted upon by the sulfonating agent.

In consideration of both productivity and uniformity of operation, the application of the aqueous dispersion of the ethylenic copolymer to the hollow fiber can be accomplished particularly effectively by either immersing the hollow fiber of the microporous membrane or resin film in the aforementioned aqueous dispersion or by causing the aqueous dispersion to flow down the inner wall surface of the hollow fiber. In this case, similarly with the case of flat membrane the desire to obtain an applied coat of the aqueous dispersion which is uniform in thickness and free from pinholes in accomplished more readily by diluting the aqueous dispersion such as with water and repetitiously applying the diluted aqueous dispersion rather than by applying just once the aqueous dispersion in its original high concentration.

When the composite film prepared in the shape of a hollow fiber by the method described above is sulfonated either directly or after being stretched as desired, the composite hydrophilic membrane in the shape of a hollow fiber can be produced.

Now, another method for the manufacture of the composite hydrophilic membrane of the present invention will be described. This method comprises producing a composite film by hot laminating at least one very thin film formed of either at least one ethylenic copolymer selected from the group consisting of an ethylenic copolymer derived from at least two monomers, ethylene and a comonomer of the general formula:

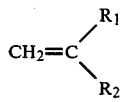

[wherein, $R_1$ denotes either H or $CH_3$ and $R_2$ denotes either $OCOR_3$ or $COOR_4$ (providing that $R_3$ is a hydrocarbon group of one to five carbon atoms and $R_4$ is H, a hydrocarbon group of one to six carbon atoms, an alkali metal, or other ion capable of forming a salt with carboxyl group)] and a saponification derivative of the ethylenic copolymer or a resin composition containing at least 15% by weight of the ethylenic copolymer mentioned above and at most 85% by weight of other thermoplastic resin and at least one polyethylenic microporous membrane or at least one polyethylenic resin film capable of being converted into a polyethylenic microporous membrane, converting the aforementioned resin film into the microporous membrane before and/or after stretching and/or during and/or after sulfonation, and causing the composite film to be reacted upon by a sulfonating agent.

In the present invention, as the ethylenic copolymer it is preferable to use, for example, a copolymer of ethylene with 1 to 18 mol % of a comonomer of the general formula:

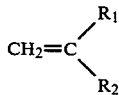

or a copolymer of ethylene with 1 to 18 mol % of a comonomer of the general formula,

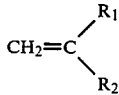

and a small amount of other comonomer.

In this case, it is imperative that the application of the film containing the aforementioned ethylenic copolymer to the aforementioned microporous membrane or resin film should be performed so that the aforementioned film or hydrophilic membrane will never peel off the microporous membrane at least prior to and/or after the sulfonation. Generally, the method of hot lamination which effects this application at temperatures in the range of about 70° to 130° C. under slight pressure proves to be particularly advantageous because the composite hydrophilic membrane can be readily obtained with high adhesive strength.

The composite hydrophilic membrane which incorporates a very thin semipermeable hydrophilic membrane as aimed at by the present invention can be produced, similarly to the method described above, by stretching the aforementioned composite film incorporating a polyethylenic microporous membrane at temperatures in the range of 50° to 130° C., for example, in which the microporous portion of the membrane can be stretched without causing thermal fusion at an area expansion ratio of at least 2, preferably at least 4, and causing the composite film to be reacted upon by a sulfonating agent.

In the case of the composite hydrophilic membrane which incorporates a polyethylenic resin film instead of the polyethylenic microporous membrane, the composite hydrophilic membrane as aimed at by this invention can be produced by causing the polyethylenic resin film to be reacted upon by the sulfonating agent before and/or after the stretching of the film and/or during and/or after the sulfonation.

This particular method of manufacture is characterized by the fact that the composite hydrophilic membrane especially abounding in resistance to oxidation degradation can be otained by allowing the film containing an ethylenic copolymer to incorporate therein at least one thermoplastic resin relatively inactive in the sulfonating agent. Examples of the thermoplastic resin useful for this purpose include polyethylene, polypropylene, 1,2-polybutadiene, and polybutene-1. Here, the amount of the thermoplastic resin to be incorporated in the film has its upper limit at 85% by weight. If the amount exceeds this upper limit, the time of the sulfonation is lengthened so much that the composite hydrophilic membrane having a high permeation rate of water may not be easily obtained. Thus, the amount is suitable below 85% by weight.

In the present method, the stretching of the composite film is necessary for producing the very thin hydrophilic membrane. This very thin hydrophilic membrane can be obtained by effecting the stretching similarly to the aforementioned method. Especially when a composition containing an ethylenic copolymer of such type as may incorporate a thermoplastic resin such as polyethylene, polypropylene, 1,2-polybutadiene, or polybutene-1 which is relatively inactive relative to the sulfonating agent is used as a hydrophilic membrane, the stretching brings about a conspicuous effect that the membrane, despite its very small thickness, will manifest lasting resistance to oxidation even after incorporation of the sulfonic group. This conspicuous effect may be logically explained by a postulate that when the composition is stretched out, the thermoplastic resin relatively inactive to the sulfonating agent is spread out therein in the shape of fibers and, consequently, the reinforcing effect of the thermoplastic resin is enhanced.

Even when the ethylenic copolymer has the aforementioned comonomer component in so small a proportion of, say, less than 3 mol % that the ethylenic copolymer cannot be effectively utilized as a sulfonated membrane by the conventional method, the present method of this invention similarly to the aforementioned method can be effectively carried out by giving a sufficiently small thickness to the film of the resin composition containing the ethylenic copolymer. Consequently, this method can produce the composite hydrophilic membrane as aimed at from the ethylenic copolymer containing the comonomer in such a small proportion as mentioned above. When the ethylenic copolymer contained in the resin composition forming the film has the comonomer component in a significantly large proportion, addition of a large amount of a polymer relatively inactive to the sulfonating agent such as, for example, polyethylene or some other polyolefin resin and/or crosslinking such as by the irradiation with electron beams proves to be advantageous for improving the film in resistance to solvents including the sulfonating agent and resistance to oxidative degradation.

By the methods described above, the composite hydrophilic membrane can be manufactured in varying shapes such as, for example, film, tube, hollow fiber, and bag and can be utilized very conveniently in a variety of applications.

Addition of an inorganic filler such as, for example, titanium dioxide or aluminum oxide to the aforementioned hydrophilic membrane and/or the aforementioned microporous membrane proves to be an effective measure for improving strength and other properties of the membrane.

Yet another method for the manufacture of the composite hydrophilic membrane of this invention will be described below. This method comprises forming a composite film incorporating (I) a polyethylenic resin composition capable of forming a microporous membrane upon being molded in the shape of a film and (II) either at least one ethylenic copolymer selected from the group consisting of an ethylenic copolymer derived from at least two monomers, ethylene and a comonomer of the general formula,

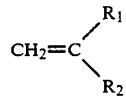

[wherein, $R_1$ denotes either H or $CH_3$ and $R_2$ denotes either $OCOR_3$ or $COOR_4$ (providing that $R_3$ is a hydrocarbon group of one to five carbon atoms and $R_4$ is H, a hydrocarbon group of one to six carbon atoms, an alkali metal, or other ion capable of forming a salt with carboxyl group)], and a saponification derivative of the aforementioned ethylenic copolymer or a resin composition containing at least 15% by weight of the aforementioned ethylenic copolymer and at most 85% by weight of other thermoplastic resin in a layer combination of (I)/(II) or (I)/(II)/(I), converting the composite film into a microporous membrane after molding and/or during and/ or after sulfonation, and sulfonating the resultant microporous membrane.

By this method, the composite film having the layer combination of (I) and (II) can be manufactured in one step by the ordinary co-extrusion molding. This method, therefore, is characterized by having high productivity.

The expression "polyethylenic resin composition capable of being converted into a microporous membrane during and/or after being molded in the shape of film" as used in this invention means the polyethylenic resin which is described in the aforementioned method of manufacture as possessing such capability. In other words, the polyethylenic resin composition which answers this description is a resin composition incorporating an extractable substance during and/or after sulfonation and forming a microporous membrane after molding of the film. Examples of such polyethylenic resin composition are polyethylene-containing resin composition which is disclosed in the aforementioned Japanese Publication of Unexamined Patent Application No. 74057/1976, a polyethylenic resin composition which incorporates an extractable inorganic or organic substance in advance and, on releasing such inorganic or organic substance, forms a microporous membrane, a polyethylene composition which, on being stretched or similarly treated, undergoes phase separation and gives birth to a microporous membrane, and a resin composition which contains polyethylene and an ethylenic copolymer. In the present invention, the formation of the microporous membrane may be properly carried out so as to suit the nature of the aforementioned resin composition (I).

Naturally in the present method, the stretching of the composite film proves to be as advantageous as in the aforementioned method.

The kind of the ethylenic copolymer and the method of the sulfonation involved in the present invention are identical with those of the aforementioned method.

In the present invention, the sulfonic group content in the very thin hydrophilic membrane and that in the microporous membrane are both based on the dry weight of the respective membranes in the potassium salt form.

The sulfonic group content, the electric resistance in alkalis, the transference number of cations, the separation factor, the permeation rate of water, the porosity of microporous membrane, the average pore diameter of microporous membrane, the area swelling ratio in alkalis, the zinc ion permeability and the electric resistance in dilute sulfuric acid which are mentioned in this invention are measured by the following methods.

Sulfonic group content (meq/gram)

This value is determined by equilibrating a given membrane of sulfonic acid ($-SO_3H$) form in a fixed volume of an aqueous 1N calcium chloride solution, titrating the hydrogen chloride produced consequently in the aqueous solution with a 0.1N aqueous sodium hydroxide solution (titer=f) with phenol phthalein as an indicator, and dividing the amount, x cc, of the titrant used by the dry weight of the membrane, w g, in its potassium salt form, thus:

$$\text{Sulfonic group content} = \frac{1/10 \cdot f \cdot x}{w} \text{ (meq/gram)}$$

Electric resistance in alkali ($\Omega \cdot cm^2$)

This value is determined by setting a given sample in position in a measuring instrument (conforming to the specification of JIS C2313) filled with an aqueous 31(weight) % potassium hydroxide solution, passing a constant direct electric current between the electrodes (nickel plates) at 23° C. at a current density of 5 mA/cm², measuring the voltage drop due to the sample on a mercuric oxide electrode, applying the relevant values found by this measurement to the following formula, and calculating the electric resistance. (Prior to the measurement, the sample is to be immersed in an aqueous 31 (weight) % potassium hydroxide solution for at least 24 hours.)

$$R_1 = \frac{(V_2 - V_1)}{0.005} \ (\Omega \cdot cm^2)$$

wherein, $R_1$ is electric resistance of the sample ($\Omega.cm^2$),
$V_1$ is voltage drop in the instrument having no sample set therein (V), and
$V_2$ is voltage drop in the instrument having a sample set therein, (V).

Transference number of cations

This value is determined by setting a given membrane in an electrolytic cell using potassium chloride as an electrolyte at concentrations of 0.2M and 0.1M on the opposite sides of the membrane, measuring the membrane potential by an ordinary method with the liquid temperature kept at 23° C., and calculating the transference number by applying the found value of membrane potential to the Nernst's formula.

Separation factor

This value is determined by setting a given sample in position in an apparatus of FIG. 1, feeding a mixture of a given organic compound with water to the feed zone of the sample by the pervaporation method*1, establishing a vacuum on the permeate zone of the sample and inducing separation of water, and calculating the factor by applying the relevant values found by the measurement to the following formula.
*1: Extra Issue 69 ('76) of "Chemistry," p. 109

Separation factor of water-organic compound, α =

$$\frac{(Weight\ percent\ of\ water\ on\ the\ permeat\ zone)/(Weight\ percent\ of\ organic\ compound\ on\ the\ permeate\ zone)}{(Weight\ percent\ of\ water\ on\ the\ feed\ zone)/(Weight\ percent\ of\ organic\ compound\ on\ the\ feed\ zone)}$$

Permeation rate of water (g/hr.m²)

This value is determined by carrying out separation of water from a given mixture by the method described above and, based on the found values, calculating the amount of water (g) passed through the membrane per unit time (hr) per unit membrane area (m²).

The meaning of this physical constant is such that when the membrane tested is used as a separation membrane, the rate of separation and the productivity of membrane separation both increase directly in proportion to the value of this constant.

Porosity of microporous membrane (%)

This value is determined by performing the calculation of the following equation.

$$Porosity\ (\%) = \frac{Total\ volume\ of\ pores}{Volume\ of\ microporous\ membrane} \times 100$$

Average pore diameter of microporous membrane (μm)

This value is determined by photographing the surface of a given microporous membrane with a scanning electron microscope, averaging major and minor diameters of each of 200 pores observed in the photomicrograph, and totaling the 200 averages and dividing the sum by 200.

Area swelling ratio in alkali (%)

This value is determined by wetting a given film (which has been thoroughly washed with water, dried in a current of hot air of 60° C. at least one hour, and retained under conditions of 23° C. of temperature and 55% of relative humidity for 24 hours) with an aqueous 31 (weight) % potassium hydroxide solution at 23° C., measuring the wet surface area $S_w$ of the film, and calculating the increase of surface area over the dry surface area $S_d$, thus:

$$Area\ swelling\ ratio\ in\ alkali = \frac{S_w - S_d}{S_d} \times 100\ (\%)$$

Zinc ion permeability (μg/hr.cm²)

This value is determined by interposing a given membrane in an electrolytic cell as a diaphragm between an aqueous solution having zinc oxide dissolved in a proportion of 40 g/liter in an aqueous 31 (weight) % potassium hydroxide solution (solution A) and an aqueous 31 (weight) % potassium hydroxide solution containing no zinc oxide (solution B), allowing the electrolytic cell thus prepared to stand in a constant temperature bath at 23° C. for 24 hours, sampling the electrolytic solution of the solution B, assaying the sample for permeated zincate ions by the atomic absorption method, calculating the amount of permeation per hour per unit area (1 cm²) of the membrane, converting the calculated amount into a zinc equivalent, and reporting the result of this conversion as zinc ion permeability (μg/hr.cm²).

Electric resistance in sulfuric acid ($\Omega.cm^2$)

This value is determined by setting a given membrane in position in a measuring instrument (conforming to the specification of JIS C2313) filled with a dilute sulfuric acid having a specific gravity of 1.2 (at 23° C.), passing a constant direct electric current between the electrodes at a current density of 25 mA/cm², measuring a voltage drop due to the interposition of the membrane, and calculating the following equation based on the found value. (Prior to the measurement, the membrane is immersed in a dilute sulfuric acid of a specific gravity of 1.2 (at 23° C.) for at least 24 hours.)

$$R_2 = \frac{(V_4 - V_3)}{0.025} \ (\Omega \cdot cm^2)$$

wherein, $R_2$ is electric resistance of the membrane in the sulfuric acid, ($\Omega.cm^2$)
$R_3$ is voltage drop in the sulfuric acid having no membrane set therein, (V) and
$R_4$ is voltage drop in the sulfuric acid having the membrane set therein, (V).

EXAMPLES 1-3

A polyethylenic microporous membrane (having 55% of porosity and 0.02 μm of average pore diameter) containing 50% by weight of finely powdered silica anhydride and having a thickness of 140 μm was formed by the ordinary method from a resin composition comprising dioctyl phthalate, finely powdered silica anhydride (having 200 m²/g of specific surface area and 16 μm of average particle diameter), and powdered high-density polyethylene (having 0.950 g/cm³ of density and 1 of MI). To the surface of the microporous membrane, an aqueous dispersion of an ethylenic copolymer (40% by weight of solid content and 0.2 μm of average particle diameter) containing —COOCH$_3$, —COOH, and —COONa groups and produced by saponifying (to a saponification degree of 95 mol %) and neutralizing (to a neutralization degree of 35 mol %) a copolymer of 93.5 mol % of ethylene and 6.5 mol % of methyl methacrylate was applied with the aid of a coating rod.

Then, the membrane was heated at 90° C. for one hour to form a complete coat of the ethylenic copolymer thereon. Another sheet of the same microporous membrane as described above was applied fast to the open side of the formed coat under pressure at a temperature of 110° C. to afford a composite film having a layer combination of microporous membrane/ethylenic copolymer/microporous membrane.

The composite film obtained as above was stretched at a temperature of 80° C. by the tenter method at an area stretching ratio of 6.25 (2.5×2.5 longitudinally and laterally), then reacted upon by fuming sulfuric acid containing 10% by weight of free sulfur trioxide at a temperature of 35° C., washed, hydrolyzed, neutralized, and otherwise treated with concentrated sulfuric acid, diluted sulfuric acid, water, and an aqueous potassium hydroxide solution, and water in the order mentioned, to afford a composite hydrophilic membrane having a very thin hydrophilic membrane adhered fast therein.

By the treatment with the aforementioned aqueous potassium hydroxide solution, most of the finely powdered silicic anhydride was extracted from the microporous membrane of the composite hydrophilic membrane. At the same time, the —COOCH$_3$ group was hydrolized and the other carboxyl groups were substantially completely converted into potassium salt of carboxylic acid and retained in the converted forms within the very thin hydrophilic membrane. The results of the treatments were as shown in Table 1. It is noted from the table that the very thin hydrophilic membrane possessed properties peculiar to a semipermeable cation-exchange membrane, that the polyethylenic microporous membrane was sulfonated, and that the tensile strength in water of the composite hydrophilic membrane was invariably over the level of 500 g/cm width.

TABLE 1

| Example No. | 1 | 2 | 3 |
|---|---|---|---|
| Time of sulfonation (minutes) | 1 | 4 | 12 |
| Thickness of very thin hydrophilic membrane (μm) | 1 | 1 | 1 |
| Sulfonic group content of very thin hydrophilic membrane (meq/gram) | 3.3 | 4.2 | 4.8 |
| Sulfonic group content of microporous membrane (meq/gram) | 0.06 | 0.08 | 0.14 |
| Electric resistance in alkali (Ω.cm²) | 0.22 | 0.10 | 0.04 |
| Transference number of cations | 0.74 | 0.62 | 0.55 |

EXAMPLES 4-6

In a apparatus for pervaporation illustrated in FIG. 1, each of the composite hydrophilic membranes obtained in Examples 1-3 was set in position and tested for separability of a mixture of 50 vol % of ethanol with water under conditions of 1 mmHg of pressure and 40° C. of temperature on the permeate zone. The results were as shown in Table 2. It is noted from the table that all the membranes showed excellent separability.

TABLE 2

| | Example No. | | |
|---|---|---|---|
| Composite hydrophilic membrane | 4 Membrane of Example 1 | 5 Membrane of Example 2 | 6 Membrane of Example 3 |
| Separation factor (α) water and ethanol | 23 | 30 | 38 |
| Permeation rate of water (Kg/hr.m²) | 5.4 | 6.0 | 7.2 |

EXAMPLE 7

The composite hydrophilic membranes obtained in Examples 1-3 were heated at 115° C. for 30 minutes. After the heating, they were found to retain their electric resistance in alkali intact and exhibit high resistance to heat.

When the polyethylenic microporous membranes used in Examples 1-3 were deprived of finely powdered silica anhydride and the resultant membranes were heated as described above, their electric resistance in alkali increased to more than 10 times the original level.

EXAMPLE 8

When the composite hydrophilic membranes of Examples 1-3 were immersed in toluene and heated at 60° C. for five hours, they retained their original weights intact, indicating that they excelled in resistance to solvents. When the polyethylenic microporous membranes used in Examples 1-3 were deprived of finely powdered silica anhydride and the resultant membranes were heated under the aforementioned conditions, they suffered loss of weight of about 20%.

EXAMPLE 9

When the composite hydrophilic membranes of Examples 1-3 were subjected to a wetting test with water, they showed almost the same degrees of surface tension as water. When the polyethylenic microporous membranes used in Examples 1-3 were deprived of finely powdered silica anhydride and the resultant membranes were subjected to the wetting test, they showed a surface tension of 33 dynes/cm, suggesting that they were devoid of hydrophilicity.

EXAMPLE 10

In the apparatus of FIG. 1, each of the composite hydrophilic membranes of Examples 1-3 was set in position and tested for separation of azeotropes of 1- propanol, 2-propanol, and acetone respectively under the conditions of 40° C. of temperature and 1 mmHg of pressure on the permeate zone. The separation factors thus found were invariably above the level of 10 and the permeation rates of water above the level of 1 kg/hr.m². The membranes provided highly selective permeation of water from the azeotropes.

EXAMPLE 11

In the apparatus of FIG. 1, each of the composite hydrophilic membranes of Examples 1–3 was set in position and used for evaporating apple juice to twice the original concentration under the conditions of 40° C. of temperature and 1 mmHg of pressure on the permeate zone. The average permeation rates of water shown by these composite hydrophilic membranes were invariably above the level of 2 kg/m².hr. Substantially all the saccharides and flavor principle of the apple juice were retained intact in the concentrated juice.

EXAMPLES 12–13

The aqueous dispersion of ethylenic copolymer used in Example 1 was diluted and the diluted aqueous dispersion was applied to the polyethylenic microporous membrane formed in Example 1. The membrane was heated at 90° C. for one hour. Thereafter, another sheet of the same microporous membrane was applied fast to the formed coat of the ethylenic copolymer under pressure at a temperature of 115° C., to afford a composite film having a layer combination of microporous membrane/ethylenic copolymer/microporous membrane.

The composite film was stretched at a temperature of 80° C. by the tenter method at an area stretching ratio of 4 (2×2 longitudinally and laterally). The stretched composite film was sulfonated under the conditions of 35° C. and five minutes by a method similar to the method of Example 1, and then subjected to the treatments of washing, hydrolysis, and neutralization. Consequently, there was obtained a composite hydrophilic membrane comprising a very thin hydrophilic membrane having a sulfonic group content of 0.08 meq/gram and a microporous membrane adhering fast to the hydrophilic membrane. When this composite hydrophilic membrane was tested for separability of a mixture of 90 vol % of ethanol with water under the same conditions as those of Examples 4–6, the results were as shown in Table 3. It is noted from the table that the membrane exhibited a high permeation rate of water from the mixture of high ethanol content, suggesting that the membrane excelled in separability. In water, the composite hydrophilic membrane showed a tensile strength of not less than 700 g/cm width.

TABLE 3

| Example No. | 12 | 13 |
| --- | --- | --- |
| Number of dilutions of aqueous dispersion | 2 | 5 |
| Thickness of very thin hydrophilic membrane (μm) | 0.8 | 0.3 |
| Sulfonic group content of very thin hydrophilic membrane (meq/gram) | 4.3 | 4.8 |
| Electric resistance in alkali (Ω.cm²) | 0.10 | 0.07 |
| Separation factor, (α) water and ethanol | 23 | 12 |
| Permeation rate of water (kg/hr.m²) | 2.0 | 3.0 |

TABLE 3-continued

| Example No. | 12 | 13 |
| --- | --- | --- |
| (kg/hr.m²) | | |

EXAMPLE 14

The aqueous dispersion of ethylenic copolymer used in Example 1 was diluted with water. The diluted aqueous dispersion was applied to one surface of the polyethylenic microporous membrane formed in Example 1. The membrane was heated at 115° C. for 30 minutes and then sulfonated by the method of Example 1 under the conditions of 35° C. and 10 minutes. It was thereafter subjected to the treatments of washing, hydrolysis, and neutralization, to afford a composite hydrophilic membrane having a layer combination of very thin hydrophilic membrane/microporous membrane, wherein the very thin hydrophilic membrane adhered fast to the microporous membrane.

The composite hydrophilic membrane was similarly tested as described above. The results were as shown in Table 4. It is noted from this table that the composite hydrophilic membrane having the aforementioned layer combination, under the same conditions as those of Examples 4–6, showed excellent separability of a mixture of 90 vol % of ethanol with water.

The sulfonic group content of the microporous membrane was 0.10 meq/gram. Similarly to the composite hydrophilic membrane of Example 1, the composite hydrophilic membrane in this example excelled in resistance to heat, resistance to solvents, and in hydrophilicity. The tensile strength of the composite hydrophilic membrane in water was over 500 g/cm width.

TABLE 4

| Example No. | 14 |
| --- | --- |
| Number of dilutions of aqueous dispersion | 2 |
| Thickness of very thin hydrophilic membrane (μm) | 3 |
| Sulfonic group content of very thin hydrophilic membrane (meq/gram) | 2.8 |
| Electric resistance in alkali (Ω.cm²) | 0.40 |
| Separation factor, (α) water and ethanol | 23 |
| Permeation rate of water (kg/hr.m²) | 0.7 |

EXAMPLE 15

In the apparatus of FIG. 1, the composite hydrophilic membrane of Example 14 was set in position. The membrane was used for dehydrating 100 cc of 1,1,1-trichloroethane containing 400 ppm of water for one hour under the conditions of 20° C. of temperature and 5 mmHg of pressure on the permeate zone. At the end of the treatment, the water content of the 1,1,1-trichloroethane was found to be 40 ppm, only one tenth of the original level. The membrane permeated only 10 mg of 1,1,1-trichloroethane. The stabilizers (dioxane, butylene oxide, and nitromethane) added to the 1,1,1-trichloroethane were retained virtually intact. Thus, the composite hydrophilic membrane was demonstrated to provide selective permeation of water from an organic solvent containing a minute proportion of water. It was also shown that the composite hydrophilic membrane could be used without producing any adverse effect upon 1,1,1-trichloroethane, an organic solvent of high solubility.

EXAMPLES 16-19

A mixture obtained by adding 5 parts by weight of isopropyl alcohol to 95 parts by weight of a latex (having 40% by weight of solids content) containing an ethylenic copolymer obtained by partially neutralizing (to a neutralization degree of 30%) of a copolymer of 95 mol % of ethylene with 5 mol % of methacrylic acid was applied with a coating rod to a microporous membrane having a thickness of 200 $\mu$m and molded by the method of Example 1. The membrane was aged by heating at 90° C. for one hour, to afford a composite film.

By a method similar to the method of Example 1, this composite film was reacted upon by a sulfonating agent, and then subjected to the treatments of washing, neutralization, washing, and drying, to produce a composite hydrophilic membrane. This membrane was similarly tested. The results were as shown in Table 5. It is noted from the table that the composite hydrophilic membrane possessed properties peculiar to a cation-exchange membrane, showed a low electric resistance, exhibited only a small area swelling property in electrolyte, and excelled in mechanical strength.

Since the microporous membrane was sulfonated, the composite hydrophilic membrane excelled in resistance to heat, resistance to solvents, and hydrophilicity similarly to the composite hydrophilic membranes of Examples 1-3.

TABLE 5

| Example No. | | 16 | 17 | 18 | 19 |
|---|---|---|---|---|---|
| Thickness of ethylenic copolymer film ($\mu$) | | 10 | 10 | 10 | 10 |
| Sulfonation conditions | Temperature (°C.) | 35 | 35 | 35 | 35 |
| | Time (minutes) | 1 | 2 | 5 | 10 |
| Sulfonic group content of very thin hydrophilic membrane (meq/gram) | | 1.5 | 2.3 | 3.2 | 3.7 |
| Sulfonic group content of microporous membrane (meq/gram) | | 0.05 | 0.06 | 0.08 | 0.10 |
| Transference number of cations | | 0.93 | 0.85 | 0.80 | 0.76 |
| Electric resistance in alkali ($\Omega.cm^2$) | | 2.2 | 0.8 | 0.5 | 0.3 |
| Area swelling ratio (%) | | 1.0 | 1.0 | 1.0 | 1.0 |
| Tensile strength in water (g/cm width) | | 800 | 800 | 800 | 800 |

EXAMPLE 20

The composite hydrophilic membranes of Examples 18-19 were tested for the ability to bar passage of Zn ions expected of separators in alkali cells using Zn electrodes represented by a Ni-Zn alkali cell. The results were as shown in Table 6. It is noted from the table that the composite hydrophilic membranes showed only very low Zn ion permeability and exhibited properties advantageous for separators in alkali cells using Zn electrodes.

TABLE 6

| Composite hydrophilic membrane | Electric resistance in alkali ($\Omega.cm^2$) | Zn ion permeability ($\mu$g/hr.cm$^2$) | Area swelling ratio in alkali (%) |
|---|---|---|---|
| Membrane of Example 18 | 0.5 | 180 | 1.0 |
| Membrane of Example 19 | 0.3 | 400 | 1.0 |

EXAMPLE 21

The composite hydrophilic membranes of Examples 16-17 were tested for electric resistance in dilute sulfuric acid required of the diaphragms in various cells using dilute sulfuric acid as an electrolyte. The results were as shown in Table 7. It is noted from the table that they showed low electric resistance in dilute sulfuric acid, excelled in resistance to heat, resistance to solvents, and hydrophilicity, and exhibited only small area swelling ratios in dilute sulfuric acid. Because of these desirable properties, they proved to be advantageously useful as diaphragms in various cells.

TABLE 7

| Composite hydrophilic membrane | Electric resistance in sulfuric acid ($\Omega.cm^2$) |
|---|---|
| Membrane of Example 16 | 0.7 |
| Membrane of Example 17 | 0.2 |

EXAMPLE 22

In a kneader, 20% by weight of a high-density polyethylene (having a density of 0.955 g/cm$^3$ and an MI of 7) was kneaded at 190° C. for 30 minutes with 80% by weight of an ethylenic copolymer (having an MI of 1) containing —COOCH$_3$, —COOH, and —COONa groups and obtained by saponifying (to a saponification degree of 60 mol %) and neutralizing (to a neutralization degree of 30 mol %) a copolymer of 94.2 mol % of ethylene with 5.8 mol % of methyl methacrylate. Then at 190° C. 1 for 30 minutes, 100 parts by weight of the resin mixture obtained as described above and 43 parts by weight of liquid paraffin (made by Kokusan Chemical Co., Ltd.) were kneaded. The resultant resin composition was extrusion molded through a die of an extruding machine at a temperature of 180° C., to afford a film 3 $\mu$m in thickness. This film was immersed in 1,1,1-trichloroethane to expel the liquid paraffin therefrom.

Separately by the conventional method, a microporous membrane was molded from a resin composition prepared, similarly to Example 1, from dioctyl phthalate, finely powdered silica anhydride, and powdered high-density polyethylene (having a density of 0.950 g/cm$^3$ and an MI of 1). This microporous membrane was treated with an aqueous potassium hydroxide solution to expel most of the finely powdered silica anhydride, to afford a microporous membrane having 65% of porosity, 0.15 $\mu$m of average pore diameter, and 200 $\mu$m of thickness. Then, the very thin film mentioned above and the microporous membrane were placed one on top of the other and adhered fast at 100° C. under pressure of about 1 kg/cm$^2$ and, thereafter, cooled. Consequently, there was obtained a composite film.

This composite film was stretched by the tenter method at a temperature of 100° C. in an area stretching ratio of 4 (2×2 longitudinally and laterally). By a method similar to the method of Example 1, the stretched composite film was sulfonated, washed, hydrolyzed, neutralized, and then dried, to afford a composite hydrophilic membrane having a layer combination of very thin hydrophilic membrane/microporous membrane. The composite hydrophilic membrane was similarly tested. The results were as shown in Table 8. It is noted from the table that the composite hydrophilic membrane retained excellent cation-exchange property even after drying, showed low electric resistance in alkali and a small area swelling ratio in alkali, excelled in resistance to heat, hydrophilicity, and tensile strength in water similarly to the composite hydrophilic membrane of Example 1, and possessed ample ability to bar passage of Zn ions. Owing to these desirable properties, the composite hydrophilic membrane proved to be advantageously usable as a separator in an Ni-Zn alkali cell.

When the composite hydrophilic membrane was tested for separability of a mixture of ethanol with water under the same conditions as those of Example 12, the separation factor was 15 and the permeation rate of water was 1 kg/hr.m$^2$, suggesting that the membrane possessed good separability.

TABLE 8

| Example No. | | 22 |
| --- | --- | --- |
| Sulfonation conditions | Temperature (°C.) | 25 |
| | Time (minutes) | 10 |
| Thickness of very thin hydrophilic membrane ($\mu$m) | | 0.75 |
| Sulfonic group content of very thin hydrophilic membrane (meq/gram) | | 2.8 |
| Sulfonic group content of microporous membrane (meq/gram) | | 0.06 |
| Electric resistance in alkali ($\Omega$.cm$^2$) | | 0.8 |
| Area swelling ratio in alkali (%) | | 1.8 |
| Transference number of cations | | 0.88 |
| Zn ion permeability ($\mu$g/hr. cm$^2$) | | 55 |
| Tensile strength in water (g/cm width) | | 550 |

EXAMPLE 23

After 14 vol % of finely powdered silica anhydride (having 200 m$^2$/g of specific surface area and 16 m$\mu$ of average particle diameter) and 64 vol % of dioctyl phthalate (DOP) were mixed and pulverized in a Henshell mixer, the resultant powdered mixture was further mixed in the same mixer with 22 vol % of a high-density polyethylene powder (having 1 of MI). The resultant mixture was kneaded and pelletized with an extruding machine.

In a kneader at 180° C., 80% by weight of a copolymer (having 8 of MI) of 92.3 mol % of ethylene with 7.7 mol % of ethyl acrylate was melted and kneaded with 20% by weight of a high-density polyethylene (having 0.955 g/cm$^3$ of density and 7 of MI). Then, 100 parts by weight of the resultant resin composition and 40 parts by weight of dioctyl phthalate were melted and mixed. The resultant mixture was cooled and then pulverized to afford a mixture containing an ethylenic copolymer. The aforementioned polyethylene resin pellets (I) and the aforementioned mixture containing the ethylenic copolymer (II) were extrusion molded by two extruders provided with multilayer dies to afford a composite film having a layer combination of (I)/(II) [wherein, the thickness of the layer (I) was 200 $\mu$m and that of the layer (II) was 40 $\mu$m].

Subsequently, the composite film was immersed in 1,1,1-trichloroethane to expel dioctyl phthalate and then stretched by the tenter at an area stretching ratio of 9. Thereafter, the stretched composite film was subjected to sulfonation, washing, hydrolysis, and neutralization. Consequently, there was obtained a composite hydrophilic membrane containing a very thin hydrophilic membrane which had a sulfonic group content of 3.8 meq/gram and a thickness of 4.5 $\mu$m and whose ethyleneacrylate copolymer had the ester group thereof substantially completely hydrolyzed.

The polyethylenic microporous membrane in this composite hydrophilic membrane had a sulfonic group content of 0.20 meq/gram, suggesting that this membrane was sufficiently sulfonated.

In the apparatus of FIG. 1, this composite hydrophilic membrane was set in position and used for evaporating tangerine juice to a concentration twice the original level at a temperature of 40° C. and under pressure of 2 mmHg on the permeate zone. In this treatment, the membrane showed at least 1 kg/hr.m$^2$ of an average permeation rate of water.

Substantially all saccharides and flavor principle of the tangerine juice were retained on the feed zone of the membrane. These results prove that the composite hydrophilic membrane is useful for the concentration of natural fruit juice having a flavor principle.

EXAMPLE 24

From the polyethylenic resin pellets (I) and the mixture containing an ethylenic copolymer (II) obtained in Example 23 were extrusion molded into two separate films. At a temperature of 120° C., these films were hot pressed to produce a composite film having a layer combination of (I)/(II) [wherein, the thickness of the layer (I) was 200 $\mu$m and that of the layer (II) was 40 $\mu$m].

By a method similar to the method of Example 23, the composite film was subjected to extraction of dioctyl phthalate, stretching, sulfonation, and other treatments, to afford a composite hydrophilic membrane substantially equal to the composite hydrophilic membrane of Example 23.

When the composite hydrophilic membrane was used for evaporating tangerine juice by following the procedure of Example 23, it proved to be useful for the concentration of natural juice containing a flavor principle.

EXAMPLE 25

From an extruding machine provided with a multilayer die, a resin composition (I) obtained from finely powdered silica anhydride impregnated with liquid paraffin and powdered high-density polyethylene (having 0.95 g/cm$^3$ of density and 1 of MI) (consisting of 40 vol % of liquid paraffin, 10 vol % of silica anhydride, and 50 vol % of high-density polyethylene) and an ethylene-vinyl acetate copolymer (II) (having 7.8 mol % of vinyl acetate content and 2.5 of MI) were extruded to produce a multilayer film having a layer combination of (I)/(II)/(I) [wherein, the thickness of each of the layers (I) is 150 $\mu$m and that of the layer (II) was 40 $\mu$m].

Subsequently, the composite film was immersed in 1,1,1-trichloroethane to extract the liquid paraffin therefrom and then stretched by the tenter at an area stretching ratio of 6.5.

The stretched composite film was subjected to sulfonation, washing, hydrolysis, neutralization, washing, and drying. Consequently, there was obtained a composite hydrophilic membrane containing a very thin hydrophilic membrane which had a sulfonic group content of 2.3 meq/gram and whose acetic ester was substantially completely hydrolyzed.

This composite hydrophilic membrane showed 0.93 of transference number of cations and 1.2 $\Omega cm^2$ of electric resistance in alkali. Because of these and other properties of the membrane, the membrane proved to be advantageously useful as a cation-exchange membrane. It was wetted quickly after it was immersed in water. In its wet condition, it exhibited high tensile strength.

EXAMPLE 26

A hollow fiber of high-density polyethylenic microporous membrane (1.4 mm of outside diameter, 0.7 mm of inside diameter, 70% of porosity, and 0.15 μm of average pore diameter) was immersed in the same aqueous dispersion of ethylenic copolymer (containing 5% by weight of ethanol) as used in Example 1 and heated at 100° C. for 30 minutes, to afford a hollow-fiber composite film having a very thin film adhered fast therein. Then, the composite film was subjected to sulfonation, washing, hydrolysis, and neutralization, to obtain a composite hydrophilic membrane. This composite hydrophilic membrane comprised a very thin hydrophilic membrane having 3 μm of thickness and 2.8 meq/gram of sulfonic group content and a polyethylenic microporous membrane having 0.06 meq/gram of sulfonic group content.

The hollow-fiber composite hydrophilic membrane thus produced showed substantially the same degree of separability of an ethanol-water mixture as the flat composite hydrophilic membrane of Example 14.

EXAMPLE 27

The composite hydrophilic membrane of Example 14 was immersed in a 1N aqueous HCl solution for about one hour and washed with water. The resultant membrane was set in position in the apparatus of FIG. 1. The membrane was used for esterification by adding ethanol and acetic acid of the same mol % in the feed zone under the conditions of 60° C. of temperature and 2 mmHg of pressure on the permeate zone.

The permeated solution was water for the most part and the fed solution contained ethyl acetate, ethanol, acetic acid and water in 0.7, 2.0, 1.9 and 0.3 mol, respectively. Thus, it was proved that the composite hydrophilic membrane is effective as a catalyst for esterification, and the water obtained by the esterification was due to separation from the reaction solution with high selectivity.

COMPARATIVE EXAMPLE 1

Sulfonation of the very thin film containing an ethylenic copolymer obtained in Example 22 was attempted by following the procedure of Example 22. When this film was taken out of the bath of fuming sulfuric acid, however, it was broken. Thus, a very thin hydrophilic membrane aimed at could not be obtained.

COMPARATIVE EXAMPLE 2

The resin composition containing an ethylenic copolymer obtained in Example 22 was extruded by following the procedure of Example 22 to produce a film 40 μm in thickness. This film was treated by the same method as that of Example 22, to afford a hydrophilic membrane having a sulfonic group content of 2.3 meq/gram.

When this hydrophilic membrane was tested for separability under the same conditions as those of Example 22, it showed 50 g/m².hr of permeation rate of water. This value is significantly smaller than the value found for the composite hydrophilic membrane of Example 22.

What is claimed is:

1. A composite hydrophilic membrane comprising at least two layers, adhered fast, formed of a very thin semipermeable hydrophilic membrane, the thickness being in the range of 0.05 to 5μ, derived from an ethylenic copolymer or an ethylenic copolymer resin composition and containing at least one hydrophilic group selected from the class consisting of —OH group and —COOR group (wherein, R is hydrogen, a hydrocarbon group of one to five carbon atoms, an alkali metal atom or other ion capable of forming a salt with carboxyl group) and at least 0.2 meq/g of sulfonic group, and a polyethylenic microporous membrane containing a sulfonic group, said composite hydrophilic membrane having the separation factor A/B (A=water and B=ethanol) of above 10 and the permeation rate of water of above 500 g/hr.m².

2. A composite hydrophilic membrane according to claim 1, wherein the ethylenic copolymer is a copolymer derived from at least two monomers, ethylene and 1-18 mol % of a comonomer of the general formula,

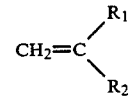

and a saponification derivatives of ethylenic copolymer.

3. A composite hydrophilic membrane according to claim 1, wherein the ethylenic copolymer resin composition is a resin composition containing at least 15% by weight of the ethylenic copolymer and at most 85% by weight of other thermoplastic resin.

4. A composite hydrophilic membrane according to claim 2, wherein the ethylenic copolymer is at least one ethylenic copolymer selected from the group consisting of ethylenevinyl acetate copolymer, saponification product of ethylenevinyl acetate copolymer, ethylene-methyl methacrylate copolymer, ethylene methacrylic acid copolymer, metal salts of ethylene-methacrylic acid copolymer, metal salts of ethylene-methyl methacrylate-methacrylic acid copolymer, ethylene-ethyl acrylate copolymer, ethylene-acrylic acid copolymer, and metal salts of ethylene-acrylic acid copolymer.

5. A composite hydrophilic membrane according to claim 3, wherein the other thermoplastic resin is at least one thermoplastic resin selected from the group consisting of polyethylene, polypropylene, 1,2-polybutadiene, and polybutene-1.

6. A composite hydrophilic membrane according to claim 1, wherein the very thin, semipermeable hydrophilic membrane contains 1 to 5 meq/gram of sulfonic group.

7. A composite hydrophilic membrane according to claim 1, wherein the sulfonic group content of the polyethylenic microporous membrane is at least 0.05 meq/gram.

8. A composite hydrophilic membrane according to any one of claims 2-5, wherein the sulfonic group content of the polyethylenic microporous membrane is at least 0.05 meq/gram.

9. A composite hydrophilic membrane according to claim 1, wherein the polyethylenic microporous membrane has an average pore diameter of the surface openings in the range of 0.01 to 1 μm.

10. A composite hydrophilic membrane according to any of claims 2-7, polyethylenic microporous membrane has an average pore diameter of the surface openings in the range of 0.01 to 1 μm.

11. A composite hydrophilic membrane according to claim 1, wherein the the polyethylenic microporous membrane has a porosity of 20-80%.

12. A composite hydrophilic membrane according to claim 1, wherein the thickness of the very thin hydrophilic membrane is not more than 1 μm.

13. A composite hydrophilic membrane according to any of claims 1-7, 9, 11 and 12, wherein the composite hydrophilic membrane has the shape of a hollow fiber, bag, spiral or flat sheet and the thickness of the composite hydrophilic membrane is between 10 μm and 1 mm.

14. A method for the manufacture of a composite hydrophilic membrane, which comprises preparing an aqueous dispersion containing an ethylenic copolymer derived from at least two monomers, ethylene and a comonomer of the general formula:

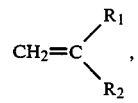

wherein, $R_1$ denotes H or $CH_3$ and $R_2$ denotes either $OCOR_3$ or $COOR_4$, provided that $R_3$ is a hydrocarbon group of one to five carbon atoms and $R_4$ is H, a hydrocarbon group of one to six carbon atoms, an alkali metal atom, or other ion capable of forming a salt with carboxyl group, applying this aqueous dispersion to a polyethylenic microporous membrane or a polyethylenic resin film, allowing the applied layer of said ethylenic copolymer to adhere fast to said microporous membrane or said resin film to form a composite film, and causing said composite film to be reacted upon by a sulfonating agent; said composite film, prior to sulfonation, may additionally be laminated to any one of, said composite film, itself, said microporous membrane, and said resin film; further, when said resin film is present in the composite, said resin film is converted, at a point after the application of the aqueous dispersion, into a microporous membrane.

15. A method for the manufacture of a composite hydrophilic membrane according to claim 14, wherein the ethylenic copolymer is a copolymer derived from at least two monomers, ethylene and 1 to 18 mol % of a comonomer of the general formula

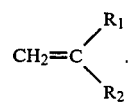

16. A method for the manufacture of a composite hydrophilic membrane according to claim 14, wherein said composite film is stretched and subsequently caused to react with a sulfonating agent.

17. A method for the manufacture of a composite hydrophilic membrane according to claim 14, wherein the composite film is stretched at an area stretching ratio of at least 2.

18. A method for the manufacture of a composite hydrophilic membrane according to any of claims 14-17, wherein the composite hydrophilic membrane has the shape of a hollow fiber.

19. A method for the manufacture of a composite hydrophilic membrane, which comprises hot laminating and stretching at least one very thin film of either at least one ethylenic copolymer selected from the group consisting of an ethylenic copolymer derived from at least two monomers, ethylene and a comonomer of the general formula:

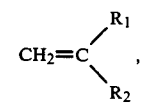

wherein, $R_1$ denotes H or $CH_3$ and $R_2$ denotes either $OCOR_3$ or $COOR_4$, provided that $R_3$ is a hydrocarbon group of one to five carbon atoms and $R_4$ is H, a hydrocarbon group of one to six carbon atoms, an alkali metal atom, or other ion capable of forming a salt with carboxyl group, and a saponification derivative of said ethylenic copolymer or a resin composition containing at least 15% by weight of said ethylenic copolymer and at most 85% by weight of another thermoplastic resin and at least one layer of a polyethylenic microporous membrane or a polyethylenic resin film capable of being converted into a polyethylenic microporous membrane, thereby producing a composite film, causing said composite film to react with a sulfonating agent and, when said polyethylenic resin film is present in the composite, said resin film is converted into a polyethylenic microporous membrane at a point after lamination.

20. A method for the manufacture of a composite hydrophilic membrane according to claim 19, wherein the ethylenic copolymer is a copolymer derived from at least two monomers, ethylene and 1 to 18 mol % of a comonomer of the general formula,

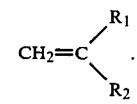

21. A method for the manufacture of a composite hydrophilic membrane according to claim 19 or 20, wherein the stretching is made at an area stretching ratio of at least 2.

22. A method for the manufacture of a composite hydrophilic membrane, which comprises joining and molding: (a) a polyethylenic resin composition (I) capable of being converted, on being molded in the shape of a film or a sheet, into a microporous membrane and (b) a resin composition (II) containing either; at least one ethylenic copolymer selected from the group consisting of an ethylenic copolymer derived from at least two monomers, ethylene and a comonomer of the general formula:

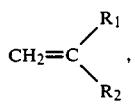

wherein, $R_1$ denotes H or $CH_3$ and $R_2$ denotes either $OCOR_3$ or $COOR_4$, provided that $R_3$ is a hydrocarbon group of one to five carbon atoms and $R_4$ is H, a hydrocarbon group of one to six carbon atoms, an alkali metal atom, or other ion capable of forming a salt with a carboxyl group; and a saponification derivative of said ethylenic copolymer or a resin composition containing at least 15% by weight of said ethylenic copolymer and at most 85% by weight of another thermoplastic resin and at least one layer of a polyethylenic microporous membrane or a polyethylenic resin film capable of being converted into a polyethylenic microporous membrane, thereby producing a composite film having a layer combination of (I)/(II) or (I)/(II)/(I), sulfonating said composite film and converting said layer of resin composition (I), at a point after molding into a microporous membrane.

23. A method for the manufacture of a composite hydrophilic membrane according to claim 22, wherein the ethylenic copolymer is a copolymer derived from at least two monomers, ethylene and 1 to 18 mol % of a comonomer of the general formula

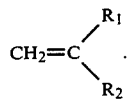

24. A method for the manufacture of a composite hydrophilic membrane according to claim 22, wherein said composite film is stretched and thereafter sulfonated.

25. A method for the manufacture of a composite hydrophilic membrane according to any one of claims 22-24, wherein the stretching is made at an area stretching ratio of at least 2.

* * * * *